United States Patent
Bonnafous et al.

(10) Patent No.: US 12,084,498 B2
(45) Date of Patent: Sep. 10, 2024

(54) COMPOUND THAT SPECIFICALLY BINDS TO KIR3DL2 FOR USE IN THE TREATMENT OF PERIPHERAL T CELL LYMPHOMA

(71) Applicant: INNATE PHARMA, Marseilles (FR)

(72) Inventors: Cécile Bonnafous, Marseilles (FR); Hélène Sicard, Marseilles (FR); Renaud Buffet, Boulogne (FR)

(73) Assignee: INNATE PHARMA, Marseilles (FR)

( * ) Notice: Subject to any disclaimer, the term of this patent is extended or adjusted under 35 U.S.C. 154(b) by 120 days.

(21) Appl. No.: 17/388,052

(22) Filed: Jul. 29, 2021

(65) Prior Publication Data

US 2021/0363248 A1 Nov. 25, 2021

Related U.S. Application Data

(60) Continuation of application No. 16/240,906, filed on Jan. 7, 2019, now Pat. No. 11,078,275, which is a continuation of application No. 15/623,572, filed on Jun. 15, 2017, now Pat. No. 10,174,112, which is a division of application No. 14/769,158, filed as application No. PCT/EP2014/053340 on Feb. 20, 2014, now abandoned.

(60) Provisional application No. 61/831,809, filed on Jun. 6, 2013, provisional application No. 61/766,798, filed on Feb. 20, 2013.

(51) Int. Cl.
*C07K 16/28* (2006.01)
*A61K 39/00* (2006.01)
*C07K 16/30* (2006.01)
*G01N 33/574* (2006.01)

(52) U.S. Cl.
CPC ...... *C07K 16/2803* (2013.01); *C07K 16/3023* (2013.01); *C07K 16/3061* (2013.01); *G01N 33/57426* (2013.01); *A61K 2039/505* (2013.01); *C07K 2317/33* (2013.01); *C07K 2317/34* (2013.01); *C07K 2317/732* (2013.01); *G01N 2333/705* (2013.01); *G01N 2333/70503* (2013.01)

(58) Field of Classification Search
None
See application file for complete search history.

(56) References Cited

U.S. PATENT DOCUMENTS

| | | |
|---|---|---|
| 5,599,790 A | 2/1997 | Altieri et al. |
| 7,153,507 B2 | 12/2006 | van de Winkel et al. |
| 7,399,595 B2 | 7/2008 | Bensussan et al. |
| 7,411,045 B2 | 8/2008 | Serrero et al. |
| 7,605,237 B2 | 10/2009 | Stevens et al. |
| 7,919,085 B2 | 4/2011 | Bensussan et al. |
| 8,119,775 B2 | 2/2012 | Moretta et al. |
| 8,222,376 B2 | 7/2012 | Padkaer et al. |
| 8,268,308 B2 | 9/2012 | Bensussan et al. |
| 8,518,655 B2 | 8/2013 | Bensussan et al. |
| 8,603,478 B2 | 12/2013 | Whalen et al. |
| 9,181,341 B2 | 11/2015 | Anfossi et al. |
| 9,828,427 B2 | 11/2017 | Anfossi et al. |
| 10,174,112 B2 | 1/2019 | Bonnafous et al. |
| 10,246,510 B2 | 4/2019 | Gauthier et al. |
| 10,280,222 B2 | 5/2019 | Gauthier et al. |
| 10,577,419 B2 | 3/2020 | Gauthier et al. |
| 11,066,470 B2 | 7/2021 | Gauthier et al. |
| 11,078,275 B2 | 8/2021 | Bonnafous et al. |
| 11,858,990 B2 | 1/2024 | Gauthier et al. |
| 2012/0064081 A1 | 3/2012 | Anfossi et al. |
| 2012/0282285 A1 | 11/2012 | Garred et al. |
| 2015/0232556 A1 | 8/2015 | Gauthier et al. |
| 2015/0291692 A1 | 10/2015 | Gauthier et al. |
| 2016/0002345 A1 | 1/2016 | Bonnafous et al. |
| 2019/0248895 A1 | 8/2019 | Paturel et al. |
| 2019/0276536 A1 | 9/2019 | Gauthier et al. |
| 2020/0199228 A1 | 6/2020 | Gauthier et al. |
| 2021/0087270 A1 | 3/2021 | Paturel et al. |
| 2021/0355213 A1 | 11/2021 | Abdelazim et al. |

FOREIGN PATENT DOCUMENTS

| | | |
|---|---|---|
| EP | 2 290 078 | 3/2011 |
| WO | WO 01/22972 | 4/2001 |
| WO | WO 02/50122 | 6/2002 |
| WO | WO 2007/071829 | 6/2007 |
| WO | WO 2010/081890 | 7/2010 |
| WO | WO 2014/191936 | 12/2014 |

OTHER PUBLICATIONS

Bouaziz, J.D. et al. "Circulating Natural Killer Lymphocytes Are Potential Cytotoxic Effectors Against Autologous Malignant Cells in Sezary Syndrome Patients" *The Journal of Investigative Dermatology*, Dec. 2005, vol. 125, No. 6, pp. 1273-1278.

Foss, F. "Evolving therapy of peripheral T-cell lymphoma: 2010 and beyond" *Therapeutic Advances in Hematology*, 2011, vol. 2, No. 3, pp. 161-173.

Ortonne, N. et al. "Significance of circulating T-cell clones in Sézary syndrome" *Blood*, May 15, 2006, vol. 107, No. 10, pp. 4030-4038.

Yamamoto, K. et al. "Phase I Study of KW-0761, a Defucosylated Humanized Anti-CCR4 Antibody, in Relapsed Patients With Adult T-Cell Leukemia-Lymphoma and Peripheral T-Cell Lymphoma" *Journal of Clinical Oncology*, Mar. 20, 2010, vol. 28, No. 9, pp. 1591-1598.

(Continued)

*Primary Examiner* — Ruixiang Li
(74) *Attorney, Agent, or Firm* — SALIWANCHIK, LLOYD & EISENSCHENK

(57) ABSTRACT

The present invention relates to methods for the treatment, prevention and diagnosis of peripheral T cell lymphoma using compounds that specifically bind KIR3DL2. The invention also relates to use of antibodies that specifically bind KIR3DL2 in diagnostic and theranostic assays in the detection and treatment of peripheral T cell lymphoma.

13 Claims, 3 Drawing Sheets
Specification includes a Sequence Listing.

(56) References Cited

OTHER PUBLICATIONS

Slater, D.N., "The new World Health Organization-European Organization for Research and Treatment of Cancer classification for cutaneous lymphomas: a practical marriage of two giants," *British Journal of Dermatology*, 2005, vol. 153, pp. 874-880.
Matsuoka, M. et al. "Treatment and prognosis of adult T cell leukemia-lymphoma" 2012, https://web.archive.org/.../20120723084215/http://www.uptodate.com/contents/treatment-and-prognosis-of-adult-t-cell-leukemia-lymphoma, downloaded Sep. 13, 2017, pp. 1-15.
Memorandum of Robert W. Bahr of Feb. 22, 2018, pp. 1-2.
Claims as filed for U.S. Appl. No. 17/114,835, filed Dec. 8, 2020, pp. 1-4.
Lloyd, C. et al. "Modelling the human immune response: performance of a $10^{11}$ human antibody repertoire against a broad panel of therapeutically relevant antigens" *Protein Engineering, Design & Selection*, 2009, pp. 159-168, vol. 22, No. 3.
Claims pending in U.S. Appl. No. 18/285,668, filed Oct. 5, 2023, p. 1.
Claims pending in U.S. Appl. No. 18/396,776, filed Oct. 5, 2023, pp. 1-3.

Sézary patient skin biopsy

12B11, 5 µg/ml mIgG1 Isotype control

AZ158, 5 µg/ml

SEQUENCE LISTING

<160> NUMBER OF SEQ ID NOS: 42

<210> SEQ ID NO 1
<211> LENGTH: 434
<212> TYPE: PRT
<213> ORGANISM: homo sapiens

<400> SEQUENCE: 1

```
Leu Met Gly Gly Gln Asp Lys Pro Phe Leu Ser Ala Arg Pro Ser Thr
1               5                   10                  15

Val Val Pro Arg Gly Gly His Val Ala Leu Gln Cys His Tyr Arg Arg
            20                  25                  30

Gly Phe Asn Asn Phe Met Leu Tyr Lys Glu Asp Arg Ser His Val Pro
        35                  40                  45

Ile Phe His Gly Arg Ile Phe Gln Glu Ser Phe Ile Met Gly Pro Val
    50                  55                  60

Thr Pro Ala His Ala Gly Thr Tyr Arg Cys Arg Gly Ser Arg Pro His
65                  70                  75                  80

Ser Leu Thr Gly Trp Ser Ala Pro Ser Asn Pro Leu Val Ile Met Val
                85                  90                  95

Thr Gly Asn His Arg Lys Pro Ser Leu Leu Ala His Pro Gly Pro Leu
            100                 105                 110

Leu Lys Ser Gly Glu Thr Val Ile Leu Gln Cys Trp Ser Asp Val Met
        115                 120                 125

Phe Glu His Phe Phe Leu His Arg Asp Gly Ile Ser Glu Asp Pro Ser
    130                 135                 140

Arg Leu Val Gly Gln Ile His Asp Gly Val Ser Lys Ala Asn Phe Ser
145                 150                 155                 160

Ile Gly Pro Leu Met Pro Val Leu Ala Gly Thr Tyr Arg Cys Tyr Gly
                165                 170                 175

Ser Val Pro His Ser Pro Tyr Gln Leu Ser Ala Pro Ser Asp Pro Leu
            180                 185                 190

Asp Ile Val Ile Thr Gly Leu Tyr Glu Lys Pro Ser Leu Ser Ala Gln
        195                 200                 205

Pro Gly Pro Thr Val Gln Ala Gly Glu Asn Val Thr Leu Ser Cys Ser
    210                 215                 220

Ser Trp Ser Ser Tyr Asp Ile Tyr His Leu Ser Arg Glu Gly Glu Ala
225                 230                 235                 240

His Glu Arg Arg Leu Arg Ala Val Pro Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg Ala Leu Pro Cys Val Trp Ser Asn Ser Ser Asp
        275                 280                 285

Pro Leu Leu Val Ser Val Thr Gly Asn Pro Ser Ser Ser Trp Pro Ser
    290                 295                 300

Pro Thr Glu Pro Ser Ser Lys Ser Gly Ile Cys Arg His Leu His Val
305                 310                 315                 320

Leu Ile Gly Thr Ser Val Val Ile Phe Leu Phe Ile Leu Leu Leu Phe
                325                 330                 335

Phe Leu Leu Tyr Arg Trp Cys Ser Asn Lys Lys Asn Ala Ala Val Met
            340                 345                 350

Asp Gln Glu Pro Ala Gly Asp Arg Thr Val Asn Arg Gln Asp Ser Asp
        355                 360                 365
```

```
Glu Gln Asp Pro Gln Glu Val Thr Tyr Ala Gln Leu Asp His Cys Val
    370                 375                 380

Phe Ile Gln Arg Lys Ile Ser Arg Pro Ser Gln Arg Pro Lys Thr Pro
385                 390                 395                 400

Leu Thr Asp Thr Ser Val Tyr Thr Glu Leu Pro Asn Ala Glu Pro Arg
                405                 410                 415

Ser Lys Val Val Ser Cys Pro Arg Ala Pro Gln Ser Gly Leu Glu Gly
                420                 425                 430

Val Phe

<210> SEQ ID NO 2
<211> LENGTH: 455
<212> TYPE: PRT
<213> ORGANISM: homo sapiens

<400> SEQUENCE: 2

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
                20                  25                  30

Ala Arg Pro Ser Thr Val Val Pro Arg Gly Gly His Val Ala Leu Gln
            35                  40                  45

Cys His Tyr Arg Arg Gly Phe Asn Asn Phe Met Leu Tyr Lys Glu Asp
        50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
                100                 105                 110

Val Val Ile Met Val Thr Gly Asn His Arg Lys Pro Ser Leu Leu Ala
            115                 120                 125

His Pro Gly Pro Leu Leu Lys Ser Gly Glu Thr Val Ile Leu Gln Cys
        130                 135                 140

Trp Ser Asp Val Met Phe Glu His Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
                260                 265                 270

Asn Arg Thr Phe Gln Ala Asp Phe Pro Leu Gly Pro Ala Thr His Gly
            275                 280                 285

Gly Thr Tyr Arg Cys Phe Gly Ser Phe Arg Ala Leu Pro Cys Val Trp
        290                 295                 300
```

```
Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
            325                 330                 335

Arg His Leu His Val Leu Ile Gly Thr Ser Val Val Ile Phe Leu Phe
                340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
        370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
                420                 425                 430

Asn Ala Glu Pro Arg Ser Lys Val Val Ser Cys Pro Arg Ala Pro Gln
            435                 440                 445

Ser Gly Leu Glu Gly Val Phe
    450                 455

<210> SEQ ID NO 3
<211> LENGTH: 123
<212> TYPE: PRT
<213> ORGANISM: mus musculus

<400> SEQUENCE: 3

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Phe
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Asn Asp Asp Thr Ala Met Tyr Tyr Cys Ala
                85                  90                  95

Arg Gly Asn Ser Asn His Tyr Val Ser Ser Phe Tyr Tyr Phe Asp Tyr
            100                 105                 110

Trp Gly Gln Gly Thr Thr Leu Thr Val Ser Ser
        115                 120

<210> SEQ ID NO 4
<211> LENGTH: 106
<212> TYPE: PRT
<213> ORGANISM: mus musculus

<400> SEQUENCE: 4

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45
```

```
His Tyr Thr Ser Thr Leu Gln Pro Gly Ile Pro Ser Arg Phe Ser Gly
    50                  55                  60
Ser Gly Ser Gly Arg Asp Tyr Ser Phe Ser Ile Ser Asn Leu Glu Pro
65                  70                  75                  80
Glu Asp Ile Thr Thr Tyr Tyr Cys Leu Gln Tyr Asp Asn Leu Trp Thr
                85                  90                  95
Phe Gly Gly Gly Thr Lys Leu Glu Ile Lys
            100                 105

<210> SEQ ID NO 5
<211> LENGTH: 119
<212> TYPE: PRT
<213> ORGANISM: mus musculus

<400> SEQUENCE: 5

Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asn Phe
                20                  25                  30
Gly Met Asn Trp Val Lys Gln Ala Pro Gly Lys Gly Leu Lys Trp Met
            35                  40                  45
Gly Trp Ile Asn Thr Tyr Thr Gly Glu Pro Thr Tyr Ala Asp Asp Phe
    50                  55                  60
Lys Gly Arg Phe Ala Phe Ser Leu Glu Thr Ser Ala Ser Thr Ala Tyr
65                  70                  75                  80
Leu Gln Ile Asn Asn Leu Lys Asn Glu Asp Met Ala Thr Tyr Phe Cys
                85                  90                  95
Ala Arg Asn Gly Asn Phe Gly Tyr Tyr Phe Asp Tyr Trp Gly Gln Gly
            100                 105                 110
Thr Thr Leu Thr Val Ser Ser
        115

<210> SEQ ID NO 6
<211> LENGTH: 112
<212> TYPE: PRT
<213> ORGANISM: mus musculus

<400> SEQUENCE: 6

Asp Val Leu Met Thr Gln Thr Pro Leu Ser Leu Pro Val Ser Leu Gly
1               5                   10                  15
Asp Gln Ala Ser Phe Ser Cys Arg Ser Ser Gln Asn Ile Val His Ser
                20                  25                  30
Asn Gly Asn Thr Tyr Leu Glu Trp Tyr Leu Gln Lys Pro Gly Gln Ser
            35                  40                  45
Pro Ser Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Thr Arg Val Glu Ala Glu Asp Leu Gly Val Tyr Tyr Cys Phe Gln Gly
                85                  90                  95
Ser His Val Pro Phe Thr Phe Gly Ser Gly Thr Lys Leu Glu Ile Lys
            100                 105                 110

<210> SEQ ID NO 7
<211> LENGTH: 5
<212> TYPE: PRT
<213> ORGANISM: mus musculus
```

```
<400> SEQUENCE: 7

Asn Phe Gly Met Asn
1               5

<210> SEQ ID NO 8
<211> LENGTH: 6
<212> TYPE: PRT
<213> ORGANISM: mus musculus

<400> SEQUENCE: 8

Gly Tyr Thr Phe Thr Asn
1               5

<210> SEQ ID NO 9
<211> LENGTH: 10
<212> TYPE: PRT
<213> ORGANISM: mus musculus

<400> SEQUENCE: 9

Gly Tyr Thr Phe Thr Asn Phe Gly Met Asn
1               5                   10

<210> SEQ ID NO 10
<211> LENGTH: 15
<212> TYPE: PRT
<213> ORGANISM: mus musculus

<400> SEQUENCE: 10

Trp Ile Asn Thr Tyr Thr Gly Glu Pro Thr Tyr Ala Asp Asp Phe
1               5                   10                  15

<210> SEQ ID NO 11
<211> LENGTH: 8
<212> TYPE: PRT
<213> ORGANISM: mus musculus

<400> SEQUENCE: 11

Trp Ile Asn Thr Tyr Thr Gly Glu
1               5

<210> SEQ ID NO 12
<211> LENGTH: 10
<212> TYPE: PRT
<213> ORGANISM: mus musculus

<400> SEQUENCE: 12

Asn Gly Asn Phe Gly Tyr Tyr Phe Asp Tyr
1               5                   10

<210> SEQ ID NO 13
<211> LENGTH: 16
<212> TYPE: PRT
<213> ORGANISM: mus musculus

<400> SEQUENCE: 13

Arg Ser Ser Gln Asn Ile Val His Ser Asn Gly Asn Thr Tyr Leu Glu
1               5                   10                  15

<210> SEQ ID NO 14
<211> LENGTH: 7
<212> TYPE: PRT
<213> ORGANISM: mus musculus

<400> SEQUENCE: 14
```

Lys Val Ser Asn Arg Phe Ser
1               5

<210> SEQ ID NO 15
<211> LENGTH: 9
<212> TYPE: PRT
<213> ORGANISM: mus musculus

<400> SEQUENCE: 15

Phe Gln Gly Ser His Val Pro Phe Thr
1               5

<210> SEQ ID NO 16
<211> LENGTH: 112
<212> TYPE: PRT
<213> ORGANISM: mus musculus

<400> SEQUENCE: 16

Gln Leu Val Gln Ser Gly Pro Glu Leu Lys Asn Pro Gly Glu Thr Val
1               5                   10                  15

Lys Ile Ser Cys Lys Ala Ser Gly Tyr Thr Phe Thr Asn Tyr Gly Met
            20                  25                  30

Asn Trp Val Lys Gln Ala Pro Gly Lys Gly Leu Lys Trp Met Gly Trp
        35                  40                  45

Ile Asn Thr Tyr Thr Gly Glu Pro Thr Tyr Ala Asp Asp Phe Lys Gly
    50                  55                  60

Arg Phe Ala Phe Ser Leu Glu Thr Ser Ala Ser Thr Ala Tyr Leu Gln
65                  70                  75                  80

Ile Asn Asn Leu Lys Asn Glu Asp Thr Ala Thr Tyr Phe Cys Ala His
                85                  90                  95

Gly Pro Trp Leu Ala Tyr Trp Gly Gln Gly Thr Leu Val Thr Val Ser
            100                 105                 110

<210> SEQ ID NO 17
<211> LENGTH: 107
<212> TYPE: PRT
<213> ORGANISM: mus musculus

<400> SEQUENCE: 17

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Val Tyr
            20                  25                  30

Leu Ser Trp Phe Gln Gln Lys Pro Gly Lys Ser Pro Lys Thr Leu Ile
        35                  40                  45

Tyr Arg Ala Ile Arg Leu Val Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Leu Pro Tyr
                85                  90                  95

Thr Phe Gly Gly Gly Thr Lys Leu Glu Ile Glu
            100                 105

<210> SEQ ID NO 18
<211> LENGTH: 5
<212> TYPE: PRT
<213> ORGANISM: mus musculus

<400> SEQUENCE: 18

Asn Tyr Gly Met Asn
1               5

<210> SEQ ID NO 19
<211> LENGTH: 6
<212> TYPE: PRT
<213> ORGANISM: mus musculus

<400> SEQUENCE: 19

Gly Tyr Thr Phe Thr Asn
1               5

<210> SEQ ID NO 20
<211> LENGTH: 10
<212> TYPE: PRT
<213> ORGANISM: mus musculus

<400> SEQUENCE: 20

Gly Tyr Thr Phe Thr Asn Tyr Gly Met Asn
1               5                   10

<210> SEQ ID NO 21
<211> LENGTH: 17
<212> TYPE: PRT
<213> ORGANISM: mus musculus

<400> SEQUENCE: 21

Trp Ile Asn Thr Tyr Thr Gly Glu Pro Thr Tyr Ala Asp Asp Phe Lys
1               5                   10                  15
Gly

<210> SEQ ID NO 22
<211> LENGTH: 10
<212> TYPE: PRT
<213> ORGANISM: mus musculus

<400> SEQUENCE: 22

Trp Ile Asn Thr Tyr Thr Gly Glu Pro Thr
1               5                   10

<210> SEQ ID NO 23
<211> LENGTH: 6
<212> TYPE: PRT
<213> ORGANISM: mus musculus

<400> SEQUENCE: 23

Gly Pro Trp Leu Ala Tyr
1               5

<210> SEQ ID NO 24
<211> LENGTH: 11
<212> TYPE: PRT
<213> ORGANISM: mus musculus

<400> SEQUENCE: 24

Lys Ala Ser Gln Asp Ile Asn Val Tyr Leu Ser
1               5                   10

<210> SEQ ID NO 25
<211> LENGTH: 7
<212> TYPE: PRT
<213> ORGANISM: mus musculus

<400> SEQUENCE: 25

Arg Ala Ile Arg Leu Val Asp
1               5

<210> SEQ ID NO 26
<211> LENGTH: 9
<212> TYPE: PRT
<213> ORGANISM: mus musculus

<400> SEQUENCE: 26

Leu Gln Tyr Asp Glu Leu Pro Tyr Thr
1               5

<210> SEQ ID NO 27
<211> LENGTH: 455
<212> TYPE: PRT
<213> ORGANISM: homo sapiens

<400> SEQUENCE: 27

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

```
Ser Asn Ser Ser Asp Pro Leu Leu Val Ser Val Thr Gly Asn Pro Ser
305                 310                 315                 320

Ser Ser Trp Pro Ser Pro Thr Glu Pro Ser Lys Ser Gly Ile Cys
            325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
            370                 375                 380

Arg Gln Asp Ser Asp Glu Gln Asp Pro Gln Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
            420                 425                 430

Asn Ala Glu Pro Arg Ser Lys Val Ser Cys Pro Arg Ala Pro Gln
            435                 440                 445

Ser Gly Leu Glu Gly Val Phe
    450                 455

<210> SEQ ID NO 28
<211> LENGTH: 455
<212> TYPE: PRT
<213> ORGANISM: homo sapiens

<400> SEQUENCE: 28

Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Leu His Arg Glu Gly Ile
145                 150                 155                 160

Ser Glu Asp Pro Ser His Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
```

```
                210                 215                 220
Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
                260                 265                 270

Asn Arg Thr Phe Gln Ala Asp Phe Pro Leu Gly Pro Ala Thr His Gly
            275                 280                 285

Gly Thr Tyr Arg Cys Phe Gly Ser Phe Arg Ala Leu Pro Cys Val Trp
        290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Ile Phe Leu Phe
                340                 345                 350

Ile Leu Leu Leu Phe Phe Leu Leu Tyr Arg Trp Cys Ser Asn Lys Lys
            355                 360                 365

Asn Ala Ala Val Met Asp Gln Glu Pro Ala Gly Asp Arg Thr Val Asn
370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Leu Thr Asp Thr Ser Val Tyr Thr Glu Leu Pro
                420                 425                 430

Asn Ala Glu Pro Arg Ser Lys Val Val Ser Cys Pro Arg Ala Pro Gln
            435                 440                 445

Ser Gly Leu Glu Gly Val Phe
    450                 455

<210> SEQ ID NO 29
<211> LENGTH: 428
<212> TYPE: PRT
<213> ORGANISM: homo sapiens

<400> SEQUENCE: 29

Lys Pro Phe Leu Ser Ala Arg Pro Ser Thr Val Val Pro Arg Gly Gly
1               5                   10                  15

His Val Ala Leu Gln Cys His Tyr Arg Arg Gly Phe Asn Asn Phe Met
                20                  25                  30

Leu Tyr Lys Glu Asp Arg Ser His Val Pro Ile Phe His Gly Arg Ile
            35                  40                  45

Phe Gln Glu Ser Phe Ile Met Gly Pro Val Thr Pro Ala His Ala Gly
        50                  55                  60

Thr Tyr Arg Cys Arg Gly Ser Arg Pro His Ser Leu Thr Gly Trp Ser
65                  70                  75                  80

Thr Pro Ser Asn Pro Leu Val Ile Met Val Thr Gly Asn His Arg Lys
                85                  90                  95

Pro Ser Leu Leu Ala His Pro Gly Pro Leu Leu Lys Ser Gly Glu Thr
            100                 105                 110

Val Ile Leu Gln Cys Trp Ser Asp Val Met Phe Glu His Phe Phe Leu
        115                 120                 125
```

-continued

```
His Arg Glu Gly Ile Ser Glu Asp Pro Ser Arg Leu Val Gly Gln Ile
130                 135                 140

His Asp Gly Val Ser Lys Ala Asn Phe Ser Ile Gly Pro Leu Met Pro
145                 150                 155                 160

Val Leu Ala Gly Thr Tyr Arg Cys Tyr Gly Ser Val Pro His Ser Pro
                165                 170                 175

Tyr Gln Leu Ser Ala Pro Ser Asp Pro Leu Asp Ile Val Ile Thr Gly
            180                 185                 190

Leu Tyr Glu Lys Pro Ser Leu Ser Ala Gln Pro Gly Pro Thr Val Gln
        195                 200                 205

Ala Gly Glu Asn Val Thr Leu Ser Cys Ser Ser Trp Ser Ser Tyr Asp
210                 215                 220

Ile Tyr His Leu Ser Arg Glu Gly Glu Ala His Glu Arg Arg Leu Arg
225                 230                 235                 240

Ala Val Pro Lys Val Asn Arg Thr Phe Gln Ala Asp Phe Pro Leu Gly
                245                 250                 255

Pro Ala Thr His Gly Gly Thr Tyr Arg Cys Phe Gly Ser Phe Arg Ala
            260                 265                 270

Leu Pro Cys Val Trp Ser Asn Ser Ser Asp Pro Leu Leu Val Ser Val
        275                 280                 285

Thr Gly Asn Pro Ser Ser Ser Trp Pro Ser Pro Thr Glu Pro Ser Ser
290                 295                 300

Lys Ser Gly Ile Cys Arg His Leu His Val Leu Ile Gly Thr Ser Val
305                 310                 315                 320

Val Ile Phe Leu Phe Ile Leu Leu Phe Phe Leu Leu Tyr Arg Trp
                325                 330                 335

Cys Ser Asn Lys Lys Asn Ala Ala Val Met Asp Gln Glu Pro Ala Gly
            340                 345                 350

Asp Arg Thr Val Asn Arg Gln Asp Ser Asp Glu Gln Asp Pro Gln Glu
        355                 360                 365

Val Met Tyr Ala Gln Leu Asp His Cys Val Phe Ile Gln Arg Lys Ile
370                 375                 380

Ser Arg Pro Ser Gln Arg Pro Lys Thr Pro Leu Thr Asp Thr Ser Val
385                 390                 395                 400

Tyr Thr Glu Leu Pro Asn Ala Glu Pro Arg Ser Lys Val Val Ser Cys
                405                 410                 415

Pro Arg Ala Pro Gln Ser Gly Leu Glu Gly Val Phe
            420                 425
```

<210> SEQ ID NO 30
<211> LENGTH: 455
<212> TYPE: PRT
<213> ORGANISM: homo sapiens

<400> SEQUENCE: 30

```
Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Gln Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80
```

Ile Met Gly Pro Val Thr Pro Ala His Ala Gly Thr Tyr Arg Cys Arg
            85                  90                  95

Gly Ser Arg Pro His Ser Leu Thr Gly Trp Ser Ala Pro Ser Asn Pro
        100                 105                 110

Leu Val Ile Met Val Thr Gly Asn His Arg Lys Pro Ser Leu Leu Ala
    115                 120                 125

His Pro Gly Thr Leu Leu Lys Ser Gly Glu Thr Val Ile Leu Gln Cys
130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
                180                 185                 190

Tyr Arg Cys Tyr Gly Ser Val Pro His Ser Pro Tyr Gln Leu Ser Ala
            195                 200                 205

Pro Ser Asp Pro Leu Asp Ile Val Ile Thr Gly Leu Tyr Glu Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
        355                 360                 365

Asn Ala Ala Val Met Asp Gln Glu Pro Ala Gly Asp Arg Thr Val Asn
370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415

Arg Pro Lys Thr Pro Pro Thr Asp Thr Ser Val Tyr Thr Glu Leu Pro
            420                 425                 430

Asn Ala Glu Pro Arg Ser Lys Val Val Ser Cys Pro Arg Ala Pro Gln
        435                 440                 445

Ser Gly Leu Glu Gly Val Phe
    450                 455

<210> SEQ ID NO 31
<211> LENGTH: 455
<212> TYPE: PRT
<213> ORGANISM: homo sapiens

<400> SEQUENCE: 31

```
Met Ser Leu Thr Val Val Ser Met Ala Cys Val Gly Phe Phe Leu Leu
1               5                   10                  15

Gln Gly Ala Trp Pro Leu Met Gly Gly Gln Asp Lys Pro Phe Leu Ser
            20                  25                  30

Ala Arg Pro Ser Thr Val Val Pro Arg Gly Gly His Val Ala Leu Gln
        35                  40                  45

Cys His Tyr Arg Arg Gly Phe Asn Asn Phe Met Leu Tyr Lys Glu Asp
    50                  55                  60

Arg Ser His Val Pro Ile Phe His Gly Arg Ile Phe Gln Glu Ser Phe
65                  70                  75                  80

Ile Met Gly Pro Val Thr Pro Ala His Ala Gly Thr Tyr Arg Cys Arg
                85                  90                  95

Gly Ser Arg Pro His Ser Leu Thr Gly Trp Ser Ala Pro Ser Asn Pro
            100                 105                 110

Leu Val Ile Met Val Thr Gly Asn His Arg Lys Pro Ser Leu Leu Ala
        115                 120                 125

His Pro Gly Pro Leu Leu Lys Ser Gly Glu Thr Val Ile Leu Gln Cys
    130                 135                 140

Trp Ser Asp Val Met Phe Glu His Phe Phe Leu His Arg Glu Gly Ile
145                 150                 155                 160

Ser Glu Asp Pro Ser Arg Leu Val Gly Gln Ile His Asp Gly Val Ser
                165                 170                 175

Lys Ala Asn Phe Ser Ile Gly Pro Leu Met Pro Val Leu Ala Gly Thr
            180                 185                 190

Tyr Arg Cys Tyr Gly Ser Val Pro His Ser Pro Tyr Gln Leu Ser Ala
        195                 200                 205

Pro Ser Asp Pro Leu Asp Ile Val Ile Thr Gly Leu Tyr Glu Lys Pro
    210                 215                 220

Ser Leu Ser Ala Gln Pro Gly Pro Thr Val Gln Ala Gly Glu Asn Val
225                 230                 235                 240

Thr Leu Ser Cys Ser Ser Trp Ser Ser Tyr Asp Ile Tyr His Leu Ser
                245                 250                 255

Arg Glu Gly Glu Ala His Glu Arg Arg Leu Arg Ala Val Pro Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe His Ala Leu Pro Cys Val Trp
    290                 295                 300

Ser Asn Ser Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Ile Cys
                325                 330                 335

Arg His Leu His Val Leu Ile Gly Thr Ser Val Val Ile Phe Leu Phe
            340                 345                 350

Ile Leu Leu Leu Phe Phe Leu Leu Tyr Arg Trp Cys Ser Asn Lys Lys
        355                 360                 365

Asn Ala Ala Val Met Asp Gln Glu Pro Ala Gly Asp Arg Thr Val Asn
    370                 375                 380

Arg Gln Asp Ser Asp Glu Gln Asp Pro Gln Glu Val Thr Tyr Ala Gln
385                 390                 395                 400

Leu Asp His Cys Val Phe Ile Gln Arg Lys Ile Ser Arg Pro Ser Gln
                405                 410                 415
```

```
Arg Pro Lys Thr Pro Leu Thr Asp Thr Ser Val Tyr Thr Glu Leu Pro
            420                 425                 430

Asn Ala Glu Pro Arg Ser Lys Val Val Ser Cys Pro Arg Ala Pro Gln
            435                 440                 445

Ser Gly Leu Glu Gly Val Phe
            450                 455

<210> SEQ ID NO 32
<211> LENGTH: 117
<212> TYPE: PRT
<213> ORGANISM: mus musculus

<400> SEQUENCE: 32

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Ala
            20                  25                  30

Gly Met Gln Trp Val Gln Lys Thr Pro Gly Lys Gly Leu Lys Trp Ile
        35                  40                  45

Gly Trp Ile Asn Ser His Ser Gly Val Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Thr Leu Lys Asn Glu Asp Thr Ala Thr Tyr Phe Cys
                85                  90                  95

Ala Arg Gly Gly Asp Glu Gly Val Met Asp Tyr Trp Gly Gln Gly Thr
            100                 105                 110

Ser Val Thr Val Ser
        115

<210> SEQ ID NO 33
<211> LENGTH: 107
<212> TYPE: PRT
<213> ORGANISM: mus musculus

<400> SEQUENCE: 33

Asp Ile Val Met Thr Gln Ser His Lys Phe Met Ser Thr Ser Leu Gly
1               5                   10                  15

Asp Arg Val Ser Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 34
<211> LENGTH: 6
<212> TYPE: PRT
<213> ORGANISM: mus musculus

<400> SEQUENCE: 34
```

```
<210> SEQ ID NO 35
<211> LENGTH: 5
<212> TYPE: PRT
<213> ORGANISM: mus musculus

<400> SEQUENCE: 35

Thr Ala Gly Met Gln
1               5

<210> SEQ ID NO 36
<211> LENGTH: 10
<212> TYPE: PRT
<213> ORGANISM: mus musculus

<400> SEQUENCE: 36

Gly Tyr Thr Phe Thr Thr Ala Gly Met Gln
1               5                   10

<210> SEQ ID NO 37
<211> LENGTH: 16
<212> TYPE: PRT
<213> ORGANISM: mus musculus

<400> SEQUENCE: 37

Trp Ile Asn Ser His Ser Gly Val Pro Lys Tyr Ala Glu Asp Phe Lys
1               5                   10                  15

<210> SEQ ID NO 38
<211> LENGTH: 9
<212> TYPE: PRT
<213> ORGANISM: mus musculus

<400> SEQUENCE: 38

Trp Ile Asn Ser His Ser Gly Val Pro
1               5

<210> SEQ ID NO 39
<211> LENGTH: 10
<212> TYPE: PRT
<213> ORGANISM: mus musculus

<400> SEQUENCE: 39

Gly Gly Asp Glu Gly Val Met Asp Tyr Trp
1               5                   10

<210> SEQ ID NO 40
<211> LENGTH: 11
<212> TYPE: PRT
<213> ORGANISM: mus musculus

<400> SEQUENCE: 40

Lys Ala Ser Gln Asp Val Ser Thr Ala Val Ala
1               5                   10

<210> SEQ ID NO 41
<211> LENGTH: 7
<212> TYPE: PRT
<213> ORGANISM: mus musculus

<400> SEQUENCE: 41

Trp Thr Ser Thr Arg His Thr
1               5
```

(Gly Tyr Thr Phe Thr Thr continued from previous page:)

```
Gly Tyr Thr Phe Thr Thr
1               5
```

```
<210> SEQ ID NO 42
<211> LENGTH: 9
<212> TYPE: PRT
<213> ORGANISM: mus musculus

<400> SEQUENCE: 42

Gln Gln His Tyr Ser Thr Pro Trp Thr
1               5
```

COMPOUND THAT SPECIFICALLY BINDS TO KIR3DL2 FOR USE IN THE TREATMENT OF PERIPHERAL T CELL LYMPHOMA

CROSS-REFERENCE TO RELATED APPLICATIONS

This application is a continuation of U.S. application Ser. No. 16/240,906, filed Jan. 7, 2019, now U.S. Pat. No. 11,078,275, which is a continuation of U.S. application Ser. No. 15/623,572, filed Jun. 15, 2017, now U.S. Pat. No. 10,174,112, which is a divisional of U.S. application Ser. No. 14/769,158, filed Aug. 20, 2015, now abandoned, which is the U.S. national stage application of International Patent Application No. PCT/EP2014/053340, filed Feb. 20, 2014, which claims the benefit of U.S. Provisional Application No. 61/766,798, filed Feb. 20, 2013, and U.S. Provisional Application No. 61/831,809, filed Jun. 6, 2013, the disclosures of which are incorporated herein by reference in their entirety, including any drawings.

REFERENCE TO SEQUENCE LISTING

The present application is being filed along with a Sequence Listing in electronic format. The Sequence Listing is provided as a file entitled "KIR-4 PCT_ST25", created 20 Feb. 2014, which is 39 KB in size. The information in the electronic format of the Sequence Listing is incorporated herein by reference in its entirety.

FIELD OF THE INVENTION

This invention relates to the use of KIR3DL2-targeting agents for the diagnosis and treatment of aggressive lymphomas.

BACKGROUND OF THE INVENTION

Peripheral T cell non-Hodgkin's lymphomas (PTCLs) account for 15% to 20% of aggressive lymphomas and for 7% to 10% of all the non-Hodgkin's lymphomas (NHLs) in Western countries. They usually occur in middle-aged to elderly patients, and presenting features are characterized by a disseminated disease in 68% of the patients, with systemic symptoms in nearly half of them (45%), bone marrow (BM) involvement in a quarter (25.8%), and extranodal disease in a third (37%). Despite aggressive therapy, more than half the patients die of their disease. While certain distinctive disease entities have improved prognostics if treated, the prognosis for many aggressive PTCLs remains relatively unchanged by the use of second- and third-generation chemotherapy regimens and 5-year overall survival (OS) still remains between 25% and 47% for PTCL-NOS, for example.

Consequently, there is a need in the art for improved benefit to patients having PTCL.

SUMMARY OF THE INVENTION

The present inventors have discovered that KIR3DL2 is expressed on the surface of peripheral T cell lymphomas (PTCLs), particularly advanced and/or aggressive PTCLs. In KIR3DL2-positive PTCLs, membranar KIR3DL2 expression permits targeting with KIR3DL2-binding antibodies (e.g., as assessed by immunohistochemistry). KIR3DL2 is expressed on few other tissues (only on a small fraction of healthy NK and T cells), permitting KIR3DL2 to serve as a marker and target for the detection and treatment of peripheral T cell lymphomas, particularly aggressive and/or advanced T cell lymphomas, e.g., aggressive and/or advanced nodal or extranodal peripheral T cell lymphomas. Accordingly, in one embodiment, a method is provided for treating or preventing a peripheral T cell lymphoma in an individual, the method comprising administering to an individual a therapeutically active amount of a compound that binds a KIR3DL2 polypeptide. In one aspect a compound is provided that binds a KIR3DL2 polypeptide, for use in the treatment or prevention of peripheral T cell lymphomas. In one embodiment, a method is provided for treating an individual having an advanced (e.g., stage IV or more) peripheral T cell lymphoma, the method comprising administering to an individual a therapeutically active amount of a compound that binds a KIR3DL2 polypeptide. In one aspect the compound that binds a KIR3DL2 polypeptide is capable of depleting a cell that expresses KIR3DL2 at its surface, e.g., a PTCL cell that expresses KIR3DL2 on its surface. In one aspect the compound is a depleting anti-KIR3DL2 antibody. In one embodiment a compound is provided that binds a KIR3DL2 polypeptide and depletes KIR3DL2-expressing tumor cells, for use in the treatment or prevention of a PTCL in an individual. Optionally the treatment or prevention comprises administration of the compound that binds a KIR3DL2 polypeptide to an individual having a PTCL. In one embodiment of any of the therapeutic uses or PTCL treatment or prevention methods herein, the individual has an ortho-visceral extranodal PTCL, optionally wherein the ortho-visceral extranodal PTCL is a NK/T− lymphoma or an enteropathy-associated T cell lymphoma (EATL). In one embodiment of any of the therapeutic uses or PTCL treatment or prevention methods herein, the individual has an anaplastic large cell lymphoma (ALCL). In one embodiment of any of the therapeutic uses or PTCL treatment or prevention methods herein, the individual has a PTCL-NOS. In one embodiment, the treatment or prevention of a PTCL in an individual comprises:
a) determining the KIR3DL2 polypeptide status of malignant cells within the individual having a PTCL, and
b) upon a determination that the individual has KIR3DL2 polypeptides prominently expressed on the surface of malignant cells, administering to the individual said compound that binds a KIR3DL2 polypeptide.

Additionally, antibodies are provided that are particularly effective in diagnostic or prognostic assays to detect KIR3DL2 expression on tumor cells, notably in immunohistochemistry assays. The antibodies are capable of detecting membranar KIR3DL2 in cases where prior antibodies were not able to detect such KIR3DL2 expression, including with specificity over KIR3DL1.

In another embodiment a method is provided comprising a KIR3DL2 detection step to identify patients having KIR3DL2+ tumors; these patients can thereafter be treated with a KIR3DL2-binding agent. Such method permits KIR3DL2 therapy to be more precisely directed to patients without reliance on disease staging. Such method also helps permit the prevention of advanced PTCL (e.g., prevention of progressing of PTCL to an advanced stage, e.g., stage IV) because patients can be treated as KIR3DL2 appears.

In a further aspect, it has been found that patients with KIR3DL2-positive PTCL-NOS can have tumors that are CD30-negative (tumor cells do not express CD30 on their surface). Thus, methods are provided of treating a CD30-negative PTCL, e.g., a PTCL-NOS, comprising administering a compound that binds a KIR3DL2 polypeptide to a patient having CD30-negative PTCL. In another embodiment of treating an individual having a PTCL, the methods or uses comprise administering a compound that binds a KIR3DL2 polypeptide to an individual having a PTCL who is refractive to treatment with an anti-CD30 antibody. In other embodiments, when PTCLs are CD30-positive (e.g., anaplastic large cell lymphomas which broadly express CD30, certain PTCL-NOS), a compound that binds a KIR3DL2 polypeptide can be administered in combination with an anti-CD30 antibody (e.g., a depleting anti-CD30 antibody).

In one embodiment, provided is a method for detecting a peripheral T cell lymphoma in an individual, the method comprising detecting a KIR3DL2 nucleic acid or polypeptide in a biological sample (e.g., on a cell) from an individual. In one embodiment, a method is provided for detecting an aggressive or advanced (e.g., stage IV or higher) peripheral T cell lymphoma in an individual, the method comprising detecting a KIR3DL2 nucleic acid or polypeptide in a biological sample (e.g., on a cell) from an individual. A determination that a biological sample expresses KIR3DL2 indicates that the patient has a peripheral T cell lymphoma (or advanced/aggressive PTCL). In one embodiment, the method comprises determining the level of expression of a KIR3DL2 nucleic acid or polypeptide in a biological sample and comparing the level to a reference level (e.g., a value, weak cell surface staining, etc.) corresponding to a healthy individual. A determination that a biological sample expresses a KIR3DL2 nucleic acid or polypeptide at a level that is increased compared to the reference level indicates that the patient has a peripheral T cell lymphoma. Optionally, detecting a KIR3DL2 polypeptide in a biological sample comprises detecting a KIR3DL2 polypeptide expressed on the surface of a malignant lymphocyte.

In one embodiment, a method is provided comprising:
(a) determining whether an individual has an advanced and/or aggressive peripheral T cell lymphoma (e.g., stage IV); and
(b) if the individual has an advanced and/or aggressive peripheral T cell lymphoma, treating the individual with a therapeutically active amount of a compound that binds a KIR3DL2 polypeptide.

In one embodiment, a method is provided comprising: (a) determining whether an individual has a peripheral T cell lymphoma; and (b) if the individual has a peripheral T cell lymphoma, determining whether the individual has peripheral T cell lymphoma cells that express a KIR3DL2 polypeptide. The method may optionally further comprise treating the individual with a therapeutically active amount of a compound that binds a KIR3DL2 polypeptide if the individual has peripheral T cell lymphoma cells that express KIR3DL2 on their surface.

In one embodiment, a method is provided comprising:
(a) determining whether an individual has peripheral T cell lymphoma cells that express a KIR3DL2 polypeptide on their surface; and
(b) if the individual has peripheral T cell lymphoma cells that express KIR3DL2 on their surface, treating the individual with a therapeutically active amount of a compound that binds a KIR3DL2 polypeptide.

In one embodiment, a method is provided comprising treating an individual having a CD30-negative PTCL. In one embodiment, the method comprises:
(a) determining whether an individual (e.g., an individual with advanced PTCL) has peripheral T cell lymphoma cells that express CD30 on their surface, and optionally further determining whether the individual has peripheral T cell lymphoma cells that express KIR3DL2 on their surface; and (b) if the individual has peripheral T cell lymphoma cells that do not express CD30 on their surface, optionally wherein the individual has peripheral T cell lymphoma cells that express a KIR3DL2 polypeptide on their surface, treating the individual with a therapeutically active amount of a compound that binds a KIR3DL2 polypeptide.

In one embodiment, a method is provided comprising treating an individual having a CD30-positive PTCL. In one embodiment, the method comprises:
(a) determining whether an individual (e.g., an individual with advanced PTCL) has peripheral T cell lymphoma cells that express CD30 on their surface, and further determining whether the individual has peripheral T cell lymphoma cells that express KIR3DL2 on their surface; and
(b) if the individual has peripheral T cell lymphoma cells that express CD30 on their surface, and the individual has peripheral T cell lymphoma cells that express a KIR3DL2 polypeptide on their surface, treating the individual with a therapeutically active amount of a compound that binds a KIR3DL2 polypeptide and with a therapeutically active amount of an anti-CD30 antibody.

In one embodiment of any of the methods, determining whether an individual has peripheral T cell lymphoma cells that express a KIR3DL2 polypeptide comprises obtaining a biological sample from the individual that comprises peripheral T cell lymphoma cells, bringing said cells into contact with an antibody that binds a KIR3DL2 polypeptide, and detecting whether the cells express KIR3DL2 on their surface.

Optionally, in any embodiment, determining whether an individual has peripheral T cell lymphoma cells that express KIR3DL2 comprises conducting an immunohistochemistry assay, e.g., an immunohistochemistry assay comprising obtaining from an individual a biological sample that comprises tumor cells, fixing and sectioning said sample to obtain a tissue section, bringing said tissue section into contact with an antibody (e.g., an antibody that competes with antibody 12B11 for binding to a human KIR3DL2 polypeptide) and detecting expression of KIR3DL2 (e.g., detecting cells that express KIR3DL2). In one embodiment, the tissue section is a frozen tissue section. Optionally determining whether an individual has peripheral T cell lymphoma cells that express KIR3DL2 comprises conducting a flow cytometry assay. Both IHC and flow cytometry can detect surface expression of KIR3DL2.

Also provided is a method of treating a patient with a PTCL, the method comprising: a) determining the KIR3DL2 polypeptide status of malignant cells (e.g., PTCL cells) within the patient, e.g., determining whether a KIR3DL2 polypeptide is prominently expressed on the surface of said malignant cells, and b) administering a compound to the patient that specifically binds to a KIR3DL2 polypeptide that is prominently expressed in said malignant cells (e.g., prominently expressed on the surface of malignant cells). Optionally, determining the KIR3DL2 polypeptide status comprises determining whether a KIR3DL2 polypeptide is prominently expressed on the surface of said malignant cells. Optionally, determining whether a KIR3DL2 polypeptide is prominently expressed on the surface of said malignant cells comprises obtaining from the individual a biological sample that comprises peripheral T cell lymphoma cells, bringing said cells into contact with an antibody that binds a KIR3DL2 polypeptide, and detecting cells that express KIR3DL2 (e.g., determining the number or portion of cells that express KIR3DL2).

Preferably the compound that binds a KIR3DL2 polypeptide is a compound that causes the death of a KIR3DL2-expressing cell. Optionally, the compound that binds a KIR3DL2 polypeptide is a polypeptide, optionally an antibody (e.g., a monoclonal antibody), that binds a KIR3DL2 polypeptide, optionally a polypeptide or other compound that is a natural ligand of NKp46. Optionally, the antibody is a depleting antibody. Optionally, the antibody is an antibody that directs ADCC and/or CDC toward a KIR3DL2-expressing cell. Optionally, the antibody is an antibody that delivers a cytotoxic agent (e.g., a small molecule) to a KIR3DL2-expressing cell.

In one embodiment, the antibody used in any embodiment herein binds a KIR3DL2 polypeptide, optionally wherein the antibody does not substantially bind to a KIR3DL1 polypeptide and has bivalent binding affinity ($K_D$) for a human KIR3DL2 polypeptide of less than $10^{-8}$ M. In one embodiment, the antibody binds a KIR3DL2 polypeptide in its D1 domain. In one embodiment, the antibody binds a KIR3DL2 polypeptide, wherein said antibody does not substantially bind to a KIR3DL1 polypeptide, and wherein said antibody binds to at least one residue in the segment corresponding to residues 99-192 of the mature KIR3DL2 polypeptide of SEQ ID NO: 1.

In one embodiment, the antibody used herein competes for binding to a KIR3DL2 polypeptide with an antibody selected from the group consisting of:
  (a) an antibody having respectively a VH and VL region of SEQ ID NOS: 5 and 6 (19H12);
  (b) an antibody having respectively a VH and VL region of SEQ ID NOS: 16 and 17 (12B11); or
  (c) an antibody having respectively a VH and VL region of SEQ ID NOS: 33 and 34 (2B12).

Optionally, the antibody binds an epitope comprising residue P179 and/or residue S181 of the KIR3DL2 polypeptide of SEQ ID NO: 1, and/or has reduced binding to a KIR3DL2 polypeptide having a mutation at residue P179 and/or residue S181 of SEQ ID NO: 1, compared to a wild-type KIR3DL2 polypeptide of SEQ ID NO: 1.

Optionally, the antibody used herein binds an epitope comprising residues N99, H100, E130, H131, F132, V178, H180, P182, Y183 and/or Q184 of SEQ ID NO: 1, and/or has reduced binding to a KIR3DL2 polypeptide having a mutation at residues N99, H100, E130, H131, F132, V178, H180, P182, Y183 and/or Q184 of SEQ ID NO: 1, compared to a wild-type KIR3DL2 polypeptide of SEQ ID NO: 1.

Optionally, the antibody (e.g., antibody 2B12 or an antibody that competes therewith for binding to KIR3DL2) binds an epitope comprising residue I60 and/or residue G62 of the KIR3DL2 polypeptide of SEQ ID NO: 1, and/or has reduced binding to a KIR3DL2 polypeptide having a mutation at residue I60 and/or residue G62 of SEQ ID NO: 1, compared to a wild-type KIR3DL2 polypeptide of SEQ ID NO: 1. Optionally, the antibody binds an epitope comprising residues P14, S15 and/or H23 of the KIR3DL2 polypeptide of SEQ ID NO: 1, and/or has reduced binding to a KIR3DL2 polypeptide having a mutation at residues P14, S15 and/or H23 of SEQ ID NO: 1, compared to a wild-type KIR3DL2 polypeptide of SEQ ID NO: 1. Optionally, the antibody used herein binds an epitope comprising residues I60, G62, P14, S15 and/or H23 of SEQ ID NO: 1.

Optionally, the compound that binds a KIR3DL2 polypeptide is administered between once daily and once per month. Optionally, the composition is administered as monotherapy. Optionally, the composition is administered in combination with a second therapeutic agent. Optionally, the composition is administered in combination with an anti-cancer agent.

In one embodiment, a method is provided of producing a composition for the treatment of peripheral T cell lymphoma or for use in the prevention of peripheral T cell lymphoma in a mammalian subject, said method comprising the steps of: a) providing a plurality of test compositions; b) testing each compound for the ability to bind KIR3DL2 and/or cause the depletion of KIR3DL2-expressing cells; and c) selecting a compound which binds a KIR3DL2 polypeptide and/or causes the depletion of KIR3DL2-expressing cells as suitable for the treatment of peripheral T cell lymphoma or for use in the prevention of peripheral T cell lymphoma.

Optionally, the method further comprises producing a quantity of the compound selected in step c) and/or formulating a quantity of the compound selected in step c) with a pharmaceutically acceptable excipient.

Optionally, step b) further comprises testing said test composition for the ability to direct ADCC and/or CDC toward a KIR3DL2-expressing cell, e.g., a peripheral T cell lymphoma cell.

In one embodiment, provided is a method comprising: (a) determining whether an individual has a peripheral T cell lymphoma; and (b) if the individual has a peripheral T cell lymphoma, treating the individual with a therapeutically active amount of a compound that binds a KIR3DL2 polypeptide.

In one embodiment, the determination of whether an individual has a peripheral T cell lymphoma is made according to standard medical guidelines.

In one embodiment, determining whether an individual has a peripheral T cell lymphoma comprises identifying a population of abnormal cells or abnormal numbers of cells. Optionally, said identification is by flow cytometry or immunohistochemistry. Optionally, the method further comprises sorting or isolating the population of abnormal cells.

In one embodiment, determining whether an individual has a peripheral T cell lymphoma comprises detecting cytogenetic aberrations (e.g., assessing karyotype).

In one embodiment, determining whether an individual has a peripheral T cell lymphoma comprises sorting the population of abnormal cells, and contacting nucleic acid isolated from the sorted cells with one or more oligonucleotides, wherein the contacting determines the presence of a neoplastic genetic marker, thereby detecting the presence of peripheral T cell lymphoma.

In one embodiment, determining whether an individual has a peripheral T cell lymphoma comprises assessing the levels of a serum protein in the individual.

Optionally, the method further comprises a step of assessing, following treatment with a compound that binds a KIR3DL2 polypeptide, whether the individual has an amelioration in peripheral T cell lymphoma, e.g., whether the individual has decreased numbers of peripheral T cell lymphoma cells.

In one embodiment of any aspect herein, the PTCL is an aggressive and/or advanced PTCL. In one embodiment, the PTCL is aggressive non-cutaneous PTCL. In one embodiment, the PTCL is PTCL-NOS (also referred to as PTCL-U). In one embodiment, the PTCL is a nodal (e.g., primarily nodal) PTCL. In one embodiment, the PTCL is an anaplastic large cell lymphoma (ALCL), optionally an ALK-negative ALCL, optionally an ALK-positive ALCL. In one embodiment, the PTCL is an angioimmunoblastic T cell lymphoma (AITL), optionally a cutaneous AITL, optionally a non-cutaneous AITL. In one embodiment, a PTCL may be an aggressive, non-cutaneous, primarily nodal PTCL. In one embodiment, the PTCL is an extranodal (e.g., primarily extranodal) PTCL. In one example a PTCL may be an aggressive, non-cutaneous, extranodal PTCL. In one embodiment the PTCL is an ortho-visceral extranodal PTCL. In one embodiment, the PTCL is an extranodal NK/T cell lymphoma, nasal type. In one embodiment, the PTCL is an enteropathy-associated T cell lymphoma. In one embodiment, the PTCL is a hepatosplenic T cell lymphoma, optionally a hepatosplenic αβ T cell lymphoma, optionally a hepatosplenic γδ T cell lymphoma.

In one embodiment of any aspect herein, the PTCL is a CD30 positive PTCL and the anti-KIR3DL2 antibody is administered in combination with an anti-CD30 antibody. In one embodiment of any aspect herein, the PTCL is a CD4 positive PTCL and the anti-KIR3DL2 antibody is administered in combination with an anti-CD3 antibody.

In one embodiment, a method is provided for diagnosing or monitoring a PTCL in an individual, the method comprising obtaining from an individual a biological sample that comprises PTCL cells, bringing said cells into contact with an antibody that binds a human KIR3DL2 polypeptide, and detecting cells that express KIR3DL2. Optionally, the antibody that binds a KIR3DL2 polypeptide is an antibody that binds a human KIR3DL2 polypeptide but does not bind to a human KIR3DL1 polypeptide. Optionally, the antibody that binds a KIR3DL2 polypeptide competes with antibody 12B11 for binding to a human KIR3DL2 polypeptide (e.g., antibody 19H12).

In one embodiment, a method is provided for determining whether a KIR3DL2 polypeptide is expressed on the surface of a tumor cell, the method comprising obtaining from an individual a biological sample that comprises tumor cells, bringing said cells into contact with an antibody that competes with antibody 12B11 for binding to a human KIR3DL2 polypeptide (e.g., antibody 19H12), and detecting cells that express KIR3DL2.

In one embodiment, a method is provided for determining whether a KIR3DL2 polypeptide is expressed on the surface of a cell, the method comprising obtaining from an individual (e.g., an individual having a PTCL) a biological sample (e.g., a tissue sample) that comprises tumor cells, fixing and sectioning said sample to obtain a tissue section, bringing said tissue section into contact with an antibody that competes with antibody 12B11 for binding to a human KIR3DL2 polypeptide (e.g., antibody 19H12), and detecting expression of KIR3DL2 (e.g., detecting cells that express KIR3DL2). In one embodiment, the tissue section is a frozen tissue section.

In one embodiment, antibodies having advantageous uses in diagnostic and prognostic methods for PTCL and other diseases are provided. A method is provided comprising:
(a) obtaining a biological sample of cells and bringing such cells into contact with antibody 19H12 or a derivative or fragment thereof, an antibody that competes therewith for binding to KIR3DL2, or an antibody that binds residue P179 and/or residue S181 on a KIR3DL2 polypeptide, optionally wherein said antibody is labeled with a detectable moiety; and
(b) determining by flow cytometry whether said antibody binds to said cells, wherein binding indicates that the cells express KIR3DL2 on their surface.

In another embodiment, a method is provided comprising:
(a) obtaining a biological sample of cells, preparing frozen tissue sections from such cells, and bringing such sections into contact with antibody 12B11 or a derivative or fragment thereof, an antibody that competes therewith for binding to KIR3DL2, or an antibody that binds residue P179 and/or residue S181 on a KIR3DL2 polypeptide, optionally wherein said antibody is labeled with a detectable moiety; and
(b) determining whether said antibody binds to said cells, wherein binding indicates that the cells express KIR3DL2 on their surface.

The present disclosure further concerns a method for diagnosing a disease state mediated by pathogenic KIR3DL2-expressing cells, said method comprising the steps of combining with an ex vivo patient sample a composition comprising a conjugate or complex comprises an antibody that binds specifically to KIR3DL2 expressed on the surface of the pathogenic cells and an imaging agent, and detecting the pathogenic cells that express a receptor for the ligand using flow cytometry.

The present disclosure further concerns a method of determining a prognosis of a cancer by detecting cancer cells in an ex vivo patient sample, said method comprising the steps of: (a) combining with an ex vivo patient sample a composition comprising a conjugate or complex comprises an antibody (e.g., antibody 19H12) that binds specifically to KIR3DL2 expressed on the surface of the pathogenic cells and an imaging agent; (b) detecting the pathogenic cells that express a receptor for the ligand using flow cytometry; and (c) determining a prognosis for the cancer.

The present disclosure further concerns a method for quantitating pathogenic cells, said method comprising the steps of: (a) combining, with an ex vivo patient sample, a conjugate or complex which comprises (i) an antibody that binds specifically to KIR3DL2 expressed on the surface of the pathogenic cells (e.g., antibody 19H12) and (ii) an imaging agent; and (b) quantitating said pathogenic cells in the ex vivo patient sample using flow cytometry.

In any of the above flow cytometry-based methods, the antibody binds to a KIR3DL2 polypeptide on the surface of cells but not to a KIR3DL1 polypeptide. Optionally, said pathogenic cells are detected by single photon flow cytometry. Optionally, said pathogenic cells are detected by multiphoton flow cytometry. Optionally, the ex vivo patient sample is a patient body fluid. Optionally, the body fluid is selected from the group consisting of spinal fluid, lymph fluid, urine, mucus, and blood. Optionally, the pathogenic cells are CD4+ T cells. Optionally, the pathogenic cells are lymphoma cancer cells. Optionally, the cancer cells are mycosis fungoides and Sézary Syndrome cancer cells. Optionally, the antibody conjugated to an imaging agent is selected from the group consisting of anti-KIR3DL2-fluorescein, anti-KIR3DL2-Oregon Green, anti-KI R3DL2-rhodamine, anti-KIR3DL2-phycoerythrin, anti-KIR3DL2-cys-Texas Red, anti-KIR3DL2-Alexa Fluor, and anti-KIR3DL2-DyLight. Optionally, the imaging agent comprises a chromophore. Optionally, the chromophore is a fluorescent chromophore. Optionally, the chromophore comprises a compound selected from the group consisting of fluorescein, Oregon Green, rhodamine, phycoerythrin, Texas Red, DyLight 680, and Alexa Fluor 488. Optionally, the methods further comprise the step of quantitating the pathogenic cells in the ex vivo patient sample.

In any of the above flow cytometry-based methods, the antibodies optionally bind to each of the KIR3DL2 polypeptides having the amino acid sequence shown in SEQ ID NOS: 1, 27 and 29 (alleles_*002, *001 and *007, respectively). In one embodiment, the antibodies bind to each of the KIR3DL2 polypeptides having the amino acid sequence shown in SEQ ID NOS: 27 and 31 (alleles_*001 and *009, respectively). In one embodiment, the antibodies bind to each of the KIR3DL2 polypeptides having the amino acid sequence shown in SEQ ID NOS: 27, 1, 29 and 31 (alleles_*001, *002, *007 and *009, respectively). In one embodiment, the antibodies bind to each of the KIR3DL2 polypeptides having the amino acid sequence shown in SEQ ID NOS: 27, 1, 2, 28 and 29 (alleles_*001, *002, *003, *005 and *007, respectively). In one embodiment, the antibodies bind to each of the KIR3DL2 polypeptides having the amino acid sequence shown in SEQ ID NOS: 27, 1, 29 and 30 (alleles_*001, *002, *007 and *008, respectively). In one embodiment, the antibodies bind to each of the KIR3DL2 polypeptides having the amino acid sequence shown in SEQ ID NOS: 27, 1, 2, 28, 29 and 30 (alleles_*001, *002, *003, *005, *007 and *008, respectively).

In any of the above flow cytometry-based methods, the antibody binds an epitope comprising one, two, three, four, five or more of residues selected from the group consisting of M128, E130, H131, R145, V147, Q149, I150, V178, P179, H180 and S181 (with reference to SEQ ID NO: 1), and/or the antibody may or may not have reduced binding to a KIR3DL2 polypeptide having a mutation at a residue selected from the group consisting of M128, E130, H131, R145, V147, Q149, I150, V178, P179, H180 and S181 (with reference to SEQ ID NO: 1). In any of the above flow cytometry-based methods, the antibody binds an epitope comprising residues P179 and/or S181 of the KIR3DL2 polypeptide, and/or has reduced binding to a KIR3DL2 polypeptide having a mutation at residues P179 and/or S181 (with reference to SEQ ID NO: 1, e.g., a P179T, S181T mutant). In one aspect the antibody binds an epitope comprising residues V178 and/or H180 of the KIR3DL2 polypeptide, and/or has reduced binding to a KIR3DL2 polypeptide having a mutation at residues V178 and/or H180 (with reference to SEQ ID NO: 1, e.g., a V178A, H180S mutant). In one aspect the antibody binds an epitope comprising residues E130, H131 and/or R145 of the KIR3DL2 polypeptide, and/or has reduced binding to a KIR3DL2 polypeptide having a mutation at residues E130, H131 and/or R145 (with reference to SEQ ID NO: 1, e.g., an E1305, H131S, R145S mutant). In any of the above flow cytometry-based methods, the antibody is an antibody that competes with and/or comprises the heavy and/or light chain CDRs 1, 2 and/or 3 of antibody 19H12 or 12B11.

These aspects are more fully described in, and additional aspects, features, and advantages will be apparent from, the description of the invention provided herein.

DESCRIPTION OF THE INVENTION

Figure 1:
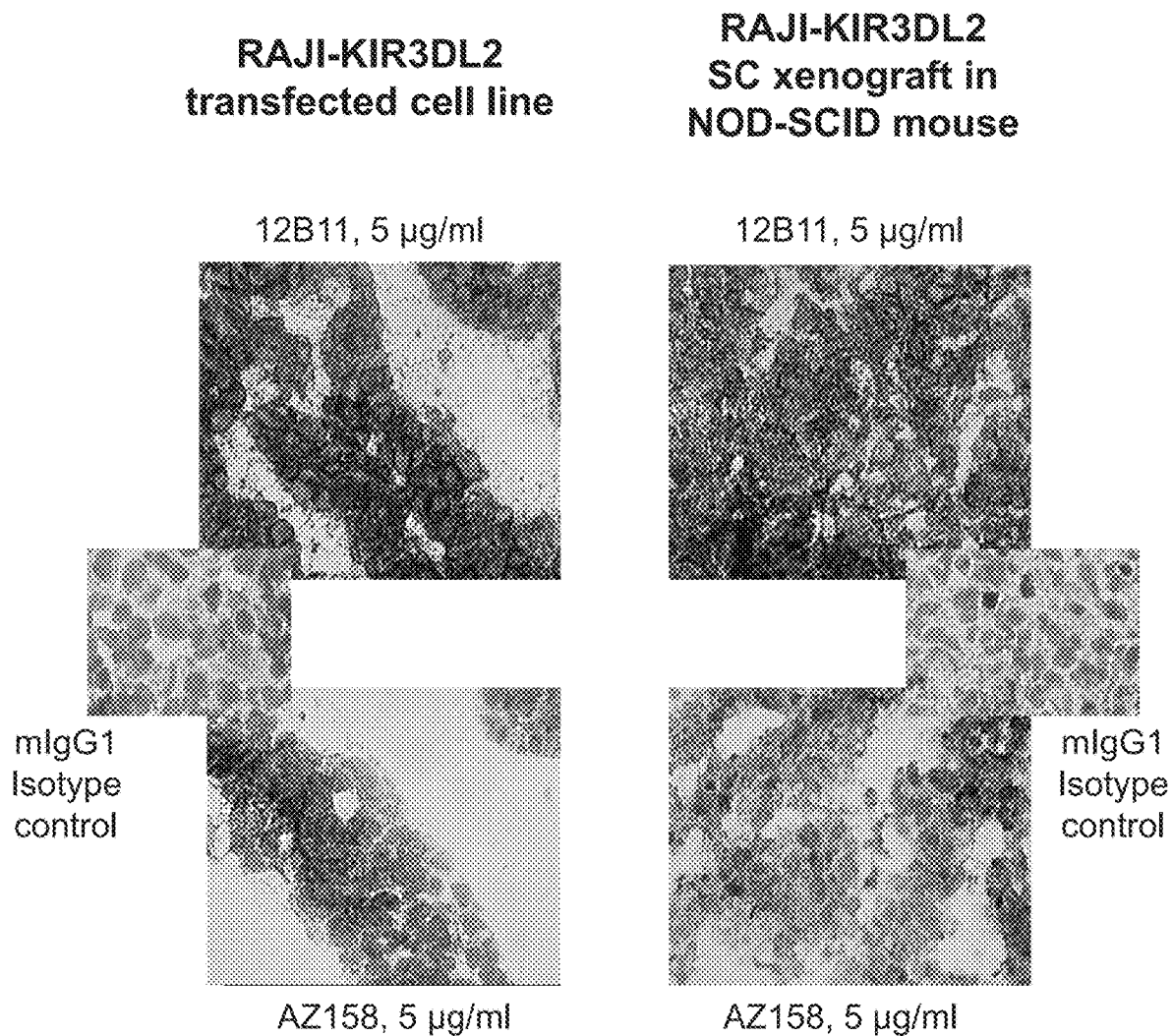
FIG. 1 shows staining of frozen tissue sections from RAJI-KIR3DL2 mouse tumor models and RAJI-KIR3DL2 cell lines, using AZ158 antibody (see WO2010/081890) or antibody 12B11. While AZ158 was negative, tumors were positive when using antibody 12B11 at the same concentration (5 µg/ml) of antibody (see FIG. 1).

The identification expression of KIR3DL2 polypeptides at the surface of malignant PTCL cells permits the development of therapeutic agents that are able to directly and specifically target pathogenic cells, as well as diagnostic agents that can be used to diagnose PTCL.

Provided are methods of using the antigen-binding compounds; for example, a method is provided for inhibiting PTCL cell proliferation or activity, for delivering a molecule to a PTCL cell (e.g., a toxic molecule, a detectable marker), for targeting, identifying or purifying a cell, for depleting, killing or eliminating a cell, or for reducing cell proliferation, the method comprising exposing a cell, such as a PTCL cell which expresses a KIR3DL2 polypeptide, to a compound that binds a KIR3DL2 polypeptide. It will be appreciated that for the purposes herein, "cell proliferation" can refer to any aspect of the growth or proliferation of cells, e.g., cell growth, cell division, or any aspect of the cell cycle. The cell may be in cell culture (in vitro) or in a mammal (in vivo), e.g., a mammal suffering from PTCL. Also provided is a method for inducing the death of a cell or inhibiting the proliferation or activity of a PTCL cell which expresses a KIR3DL2 polypeptide, comprising exposing the cell to an antigen-binding compound that binds a KIR3DL2 polypeptide in an amount effective to induce death and/or inhibit the proliferation of the cell.

Antibodies specific for KIR3DL2 can be used for a range of purposes for the diagnosis or treatment of PTCL, including purifying KIR3DL2 or KIR3DL2-expressing cells in patients having PTCL, suspected of having PTCL or susceptible to PTCL, targeting KIR3DL2-expressing cells for destruction in vivo, or specifically labeling/binding KIR3DL2 in vivo, ex vivo, or in vitro, in cells of patients having PTCL, suspected of having PTCL or susceptible to PTCL, including by methods such as immunoblotting, IHC analysis, i.e., on frozen biopsies, FACS analysis, and immunoprecipitation.

As used herein, "a" or "an" may mean one or more. As used in the claim(s), when used in conjunction with the word "comprising", the words "a" or "an" may mean one or more than one. As used herein, "another" may mean at least a second or more.

Where "comprising" is used, this can optionally be replaced by "consisting essentially of" or by "consisting of".

Whenever within this whole specification "treatment of PTCL" or the like is mentioned with reference to an anti-KIR3DL2 binding agent (e.g., an antibody), there is meant: (a) the method of treatment of PTCL, said method comprising the step of administering (for at least one treatment) an anti-KIR3DL2 binding agent, (e.g., in a pharmaceutically acceptable carrier material) to a warm-blooded animal, especially a human, in need of such treatment, in a dose that allows for the treatment of PTCL (a therapeutically effective amount), e.g., in a dose (amount) as specified hereinabove and hereinbelow; (b) the use of an anti-KIR3DL2 binding agent for the treatment of PTCL, or an anti-KIR3DL2 binding agent for use in said treatment (especially in a human); (c) the use of an anti-KIR3DL2 binding agent for the manufacture of a pharmaceutical preparation for the treatment of PTCL, or a method of using an anti-KIR3DL2 binding agent for the manufacture of a pharmaceutical preparation for the treatment of PTCL, comprising admixing an anti-KIR3DL2 binding agent with a pharmaceutically acceptable carrier, or a pharmaceutical preparation comprising an effective dose of an anti-KIR3DL2 binding agent that is appropriate for the treatment of PTCL; or (d) any combination of a), b), and c), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody" as used herein refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms "variable light chain ($V_L$)" and "variable heavy chain ($V_H$)" refer to these light and heavy chains, respectively. The heavy-chain constant domains that correspond to the different classes of immunoglobulins are termed "alpha", "delta", "epsilon", "gamma" and "mu", respectively. The subunit structures and three-dimensional configurations of different classes of immunoglobulins are well-known. IgG is the exemplary class of antibodies employed herein because they are the most common antibodies in the physiological situation and because they are the most easily made in a laboratory setting. In one embodiment, an antibody is a monoclonal antibody. Provided are humanized, chimeric, human, or otherwise human-suitable antibodies. "Antibodies" also includes any fragment or derivative of any of the herein described antibodies.

The term "specifically binds to" means that an antibody can bind in a competitive binding assay to the binding partner, e.g., KIR3DL2, as assessed using either recombinant forms of the proteins, epitopes thereof, or native proteins present on the surface of isolated target cells. Competitive binding assays and other methods for determining specific binding are further described below and are well-known in the art.

When an antibody is said to "compete with" a particular monoclonal antibody, it means that the antibody competes with the monoclonal antibody in a binding assay using either recombinant KIR3DL2 molecules or surface-expressed KIR3DL2 molecules. For example, if a test antibody reduces the binding of AZ158, 19H12, 2B12 or 12B11 to a KIR3DL2 polypeptide or KIR3DL2-expressing cell in a binding assay, the antibody is said to "compete" respectively with AZ158, 19H12, 2B12 or 12B11.

The term "affinity", as used herein, means the strength of the binding of an antibody to an epitope. The affinity of an antibody is given by the dissociation constant Kd, defined as [Ab]×[Ag]/[Ab−Ag], where [Ab−Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988; Coligan et al., eds., Current Protocols in Immunology, Greene Publishing Assoc. and Wiley Interscience, N.Y., (1992, 1993); and Muller, Meth. Enzymol. 92:589-601 (1983), which references are entirely incorporated herein by reference. One standard method well-known in the art for determining the affinity of mAbs is the use of surface plasmon resonance (SPR) screening (such as by analysis with a BIAcore™ SPR analytical device).

A "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen-binding antibody or peptide, i.e., amino acid residues within the "footprint" of the antibody. It is the simplest form or smallest structural area on a complex antigen molecule that can combine with, e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term "conformational" is therefore often used interchangeably with "structural".

The term "immunogenic fragment" refers to any polypeptidic or peptidic fragment that is capable of eliciting an immune response such as (i) the generation of antibodies binding said fragment and/or binding any form of the molecule comprising said fragment, including the membrane-bound receptor and mutants derived therefrom, or (ii) the stimulation of a T-cell response involving T cells reacting to the bi-molecular complex comprising any MHC molecule and a peptide derived from said fragment. Alternatively, an immunogenic fragment also refers to any construction capable of eliciting an immune response as defined above, such as a peptidic fragment conjugated to a carrier protein by covalent coupling, or a chimeric recombinant polypeptide construct comprising said peptidic fragment in its amino acid sequence, and specifically includes cells transfected with a cDNA of which the sequence comprises a portion encoding said fragment.

The terms "depleting", "deplete" or "depletion", with respect to KIR3DL2-expressing cells, mean a process, method, or compound that can kill, eliminate, lyse or induce such killing, elimination or lysis so as to negatively affect the number of KIR3DL2-expressing cells present in a sample or in a subject.

The terms "immunoconjugate", "antibody conjugate", "antibody drug conjugate" and "ADC" are used interchangeably and refer to an antibody that is conjugated to another moiety (e.g., any non-antibody moiety, a therapeutic agent or a label).

The term "agent" is used herein to denote a chemical compound, a mixture of chemical compounds, a biological macromolecule, or an extract made from biological materials. The term "therapeutic agent" refers to an agent that has biological activity.

The terms "toxic agent", "toxic moiety" and "cytotoxic agent" encompass any compound that can slow down, halt, or reverse the proliferation of cells, decrease their activity in any detectable way, or directly or indirectly kill them. Cytotoxic agents can cause cell death primarily by interfering directly with the cell's functioning, and include, but are not limited to, alkylating agents, tumor necrosis factor inhibitors, DNA intercalators, microtubule inhibitors, kinase inhibitors, proteasome inhibitors and topoisomerase inhibitors. A "toxic payload" as used herein refers to a sufficient amount of cytotoxic agent which, when delivered to a cell, result in cell death. Delivery of a toxic payload may be accomplished by administration of a sufficient amount of immunoconjugate comprising an antibody or antigen-binding fragment and a cytotoxic agent. Delivery of a toxic payload may also be accomplished by administration of a sufficient amount of an immunoconjugate comprising a cytotoxic agent, wherein the immunoconjugate comprises a secondary antibody or antigen-binding fragment thereof which recognizes and binds an antibody or antigen-binding fragment.

The term "human-suitable", with respect to an antibody, refers to any antibody, derivatized antibody, or antibody fragment that can be safely used in humans for, e.g., the therapeutic methods described herein. Human-suitable antibodies include all types of humanized, chimeric, or fully human antibodies, or any antibodies in which at least a portion of the antibody is derived from humans or otherwise modified so as to avoid the immune response that is generally provoked when native non-human antibodies are used.

A "humanized" or "human" antibody refers to an antibody in which the constant and variable framework region of one or more human immunoglobulins is fused with the binding region, e.g., the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen-binding site (variable region) is linked to a constant region of a different or altered class, effector function and/or species, or an entirely different molecule which confers new properties to the chimeric antibody, e.g., an enzyme, toxin, hormone, growth factor, drug, etc., or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., a, 6, c and p for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, MD).

The term "antibody-dependent cell-mediated cytotoxicity" or "ADCC" is well-understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide", "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "recombinant", when used with reference, e.g., to a cell, nucleic acid, protein, or vector, indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

As used herein, "T cells" refers to a sub-population of lymphocytes that mature in the thymus, and which display, among other molecules, T cell receptors on their surface. T cells can be identified by virtue of certain characteristics and biological properties, such as the expression of specific surface antigens including TCR, CD4 or CD8, optionally CD4 and IL-23R, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well-known in the art.

"Prominently expressed", when referring to a KIR3DL2 polypeptide, means that the KIR3DL2 polypeptide is expressed in a substantial number of tumor cells (e.g., PTCL cells, malignant or over-proliferating T or NK cells) taken from a given patient. While the definition of the term "prominently expressed" is not bound by a precise percentage value, in most cases a receptor said to be "prominently expressed" will be present on at least 30%, 40%, 50%, 60%, 70%, 80%, or more of the PTCL cells taken from a patient.

As used herein, an antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithm"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al., NCB/NLM/NIH, Bethesda, Md. 20894; Altschul et al., supra). The well-known Smith-Waterman algorithm may also be used to determine identity.

Production of Antibodies

KIR3DL2 (CD158k) is a disulfide-linked homodimer of three-Ig domain molecules of about 140 kD, described in Pende et al. (1996) J. Exp. Med. 184: 505-518, the disclosure of which is incorporated herein by reference. Several allelic variants have been reported for KIR3DL2 polypeptides; each of these are encompassed by the term KIR3DL2. The amino acid sequence of the mature human KIR3DL2 (allele *002) is shown in SEQ ID NO: 1 below, corresponding to GenBank Accession No. AAB52520, in which the 21 amino acid residue leader sequence has been omitted:

```
                                          (SEQ ID NO: 1)
LMGGQDKPF  LSARPSTVVP  RGGHVALQCH  YRRGFNNFML

YKEDRSHVPI  FHGRIFQESF  IMGPVTPAHA  GTYRCRGSRP

HSLTGWSAPS  NPLVIMVTGN  HRKPSLLAHP  GPLLKSGETV

ILQCWSDVMF  EHFFLHRDGI  SEDPSRLVGQ  IHDGVSKANF

SIGPLMPVLA  GTYRCYGSVP  HSPYQLSAPS  DPLDIVITGL

YEKPSLSAQP  GPTVQAGENV  TLSCSSWSSY  DIYHLSREGE

AHERRLRAVP  KVNRTFQADF  PLGPATHGGT  YRCFGSFRAL

PCVWSNSSDP  LLVSVTGNPS  SSWPSPTEPS  SKSGICRHLH

VLIGTSVVIF  LFILLLFFLL  YRWCSNKKNA  AVMDQEPAGD

RTVNRQDSDE  QDPQEVTYAQ  LDHCVFIQRK  ISRPSQRPKT

PLTDTSVYTE  LPNAEPRSKV  VSCPRAPQSG  LEGVF.
```

The cDNA of KIR3DL2 (allele *002) is shown in GenBank Accession No. U30272. The amino acid sequence of human KIR3DL2 allele *003 is shown below, corresponding to GenBank Accession No. AAB36593:

```
                                          (SEQ ID NO: 2)
MSLTVVSMAC  VGFFLLQGAW  PLMGGQDKPF  LSARPSTVVP

RGGHVALQCH  YRRGFNNFML  YKEDRSHVPI  FHGRIFQESF

IMGPVTPAHA  GTYRCRGSRP  HSLTGWSAPS  NPVVIMVTGN

HRKPSLLAHP  GPLLKSGETV  ILQCWSDVMF  EHFFLHREGI

SEDPSRLVGQ  IHDGVSKANF  SIGPLMPVLA  GTYRCYGSVP

HSPYQLSAPS  DPLDIVITGL  YEKPSLSAQP  GPTVQAGENV

TLSCSSWSSY  DIYHLSREGE  AHERRLRAVP  KVNRTFQADF

PLGPATHGGT  YRCFGSFRAL  PCVWSNSSDP  LLVSVTGNPS

SSWPSPTEPS  SKSGICRHLH  VLIGTSVVIF  LFILLLFFLL

YRWCSNKKNA  AVMDQEPAGD  RTVNRQDSDE  QDPQEVTYAQ

LDHCVFIQRK  ISRPSQRPKT  PLTDTSVYTE  LPNAEPRSKV

VSCPRAPQSG  LEGVF.
```

Also encompassed are any nucleic acid or protein sequences sharing one or more biological properties or functions with wild-type, full-length KIR3DL2, respectively, and sharing at least 70%, 80%, 90%, 95%, 96%, 97%, 98%, 99%, or higher nucleotide or amino acid identity.

Closely related KIR3DL1 (CD158e1) is a monomeric molecule of about 70 kD, described in Colonna and Samaridis (1995) Science 268 (5209), 405-408. The cDNA encoding a KIR3DL1 (CD158e2) polypeptide (allele *00101) is shown in GenBank Accession No. L41269; the encoded amino acid sequence is shown in GenBank Accession No. AAA69870. In one embodiment, a KIR3DL1 polypeptide referred to herein is allele *00101.

Examples of antibodies that bind human KIR3DL2 include antibody AZ158, antibody 19H12, antibody 2B12 and antibody 12B11. Further antibodies are provided in the United States patent application publication numbers 20150232556 and 20150291692, both of which are incorporated herein by reference. AZ158 binds human KIR3DL2 as well as human KIR3DL1 and KIR3DS1 polypeptides; 19H12, 2B12 and 12B11 bind selectively to KIR3DL2 and do not bind KIR3DL1 (or KIR3DS1). While antibody AZ158 can be used, for example, as a therapeutic agent administered to an individual for the elimination of a KIR3DL2-expressing target, e.g., by induction of ADCC and/or CDC, antibodies 12B11 and 19H12 will be advantageous over AZ158 for use in detection (e.g., in vitro assays) of KIR3DL2 expression on the surface of tumor cells because 12B11 and 19H12 are both able to detect KIR3DL2-positive cells in detection assays; 12B11 is advantageous for immunohistochemistry assays using frozen tissue sections, while 19H12 is advantageous for flow cytometry detection. Each of 2B12, 19H12 and 12B11 are also suitable for use as a therapeutic agent administered to an individual for the elimination of KIR3DL2-expressing target cells. 19H12 and 12B11 as well as other antibodies disclosed in the United States patent application publication number 20150291692 are capable of being internalized into cells via KIR3DL2 and can be used advantageously as an antibody-drug conjugate. 2B12 and other antibodies disclosed in the United States patent application publication 20150232556 do not induce any KIR3DL2 internalization into tumor cells, thereby providing advantageous use when effector cell-mediated activity is sought, e.g., for depleting antibodies that induce ADCC.

In a specific embodiment, an antibody is provided that binds essentially the same epitope or determinant as any of monoclonal antibodies AZ158, 19B12, 12B11 or 2B12; optionally the antibody comprises an antigen-binding region of antibody AZ158, 19B12, 12B11 or 2B12. In any of the embodiments herein, antibody AZ158, 19B12, 12B11 or 2B12 can be characterized by its amino acid sequence and/or the nucleic acid sequence encoding it. In one embodiment, the monoclonal antibody comprises the Fab or F(ab')₂ portion of AZ158, 19B12, 12B11 or 2B12. Also provided is a monoclonal antibody that comprises the heavy chain variable region of AZ158, 19B12, 12B11 or 2B12. According to one embodiment, the monoclonal antibody comprises the three CDRs of the heavy chain variable region of AZ158, 19B12, 12B11 or 2B12. Also provided is a monoclonal antibody that further comprises the light chain variable region of AZ158, 19B12, 12B11 or 2B12 or one, two or three of the CDRs of the light chain variable region of AZ158, 19B12, 12B11 or 2B12. Optionally any one or more of said light or heavy chain CDRs may contain one, two, three, four or five or more amino acid modifications (e.g., substitutions, insertions or deletions). Optionally, an antibody is provided where any of the light and/or heavy chain variable regions comprising part or all of an antigen-binding region of antibody AZ158, 19B12, 12B11 or 2812 are fused to an immunoglobulin constant region of the human IgG type, optionally a human constant region, optionally a human IgG1 or IgG3 isotype.

Antibody AZ158

AZ158 binds human KIR3DL2 as well as human KIR3DL1 polypeptides. AZ158 can be characterized as having the heavy and light chain variable regions or heavy and light chain region CDRs of SEQ ID NOS: 8 and 10, respectively, of PCT patent publication no. WO2010/081890. The VH of AZ158 is shown below, with CDRs 1, 2 and 3 underlined, respectively:

```
                                          (SEQ ID NO: 3)
QVQLKESGPG LVAPSQSLSI TCTVSGFSLT SFGVHWVRQP

PGKGLEWLGV IWAGGSTNYN SALMSRLSIS KDNSKSQVFL

KMNSLQNDDT AMYYCARGNS NHYVSSFYYF DYWGQGTTLT

VSS.
```

The VL of AZ158 is shown below with CDRs 1, 2 and 3 underlined, respectively:

```
                                          (SEQ ID NO: 4)
DIQMTQSPSS LSASLGGKVT ITCKASQDIN KYIAWYQHKP

GKGPRLLIHY TSTLQPGIPS RFSGSGSGRD YSFSISNLEP

EDITTYYCLQ YDNLWTFGGG TKLEIK.
```

The anti-KIR3DL2 antibodies may include antibodies having variable region or CDR sequences from such AZ158 antibodies (e.g., a heavy and/or light chain variable region fused to a human constant region; a heavy chain variable region fused to a human IgG1 heavy chain constant region); alternatively, the anti-KIR3DL2 antibodies may be an antibody other than the antibodies having variable region or CDR sequences from an AZ158 antibody.

Antibody 19H12

The amino acid sequence of the heavy chain variable region of antibody 19H12 is listed below:

```
                                          (SEQ ID NO: 5)
QIQLVQSGPELKKPGETVKISCKASGYTFTNFGMNWVKQAPGKGLKWMGW

INTYTGEPTYADDFKGRFAFSLETSASTAYLQINNLKNEDMATYFCARNG

NFGYYFDYWGQGTTLTVSS.
```

The amino acid sequence of the light chain variable region of antibody 19H12 is listed below:

```
                                          (SEQ ID NO: 6)
DVLMTQTPLSLPVSLGDQASFSCRSSQNIVHSNGNTYLEWYLQKPGQSPS

LLIYKVSNRFSGVPDRFSGSGSGTDFTLKITRVEAEDLGVYYCFQGSHVP

FTFGSGTKLEIK.
```

In one aspect, a purified polypeptide is provided which encodes an antibody, wherein the antibody comprises an HCDR1 region comprising an amino acid sequence GYTFTNFGMN as set forth in SEQ ID NO:9, or a sequence of at least 4, 5, 6, 7, 8, 9 or 10 contiguous amino acids thereof (e.g., NFGMN (SEQ ID NO: 7), GYTFTN (SEQ ID NO: 8)), wherein one or more of these amino acids may be substituted by a different amino acid; an HCDR2 region comprising an amino acid sequence WINTYTGEPTYADDF as set forth in SEQ ID NO: 10, or a sequence of at least 4, 5, 6, 7, 8, 9 or 10 contiguous amino acids thereof (e.g., WINTYTGE (SEQ ID NO: 11)), wherein one or more of these amino acids may be substituted by a different amino acid; an HCDR3 region comprising an amino acid sequence NGNFGYYFDY as set forth in SEQ ID NO: 12, or a sequence of at least 4, 5, 6, 7, 8, 9 or 10 contiguous amino acids thereof, wherein one or more of these amino acids may be substituted by a different amino acid; an LCDR1 region comprising an amino acid sequence RSSQNIVHSNGNTYLE as set forth in SEQ ID NO: 13, or a sequence of at least 4, 5, 6, 7, 8, 9 or 10 contiguous amino acids thereof, wherein one or more of these amino acids may be substituted by a different amino acid; an LCDR2 region comprising an amino acid sequence KVSNRFS as set forth in SEQ ID NO: 14, or a sequence of at least 4, 5, 6, 7, 8, 9 or 10 contiguous amino acids thereof, wherein one or more of these amino acids may be substituted by a different amino acid; and/or an LCDR3 region comprising an amino acid sequence FQGSHVPFT as set forth in SEQ ID NO: 15, or a sequence of at least 4, 5, 6, 7, 8, 9 or 10 contiguous amino acids thereof, wherein one or more of these amino acids may be deleted or substituted by a different amino acid, or where the sequence may comprise an insertion of one or more amino acids.

In another aspect, an antibody is provided that binds human KIR3DL2, comprising:
  (a) the heavy chain variable region of SEQ ID NO: 5, wherein one, two, three or more amino acid residues may be substituted by a different amino acid; and/or
  (b) the light chain variable region of SEQ ID NO: 6, wherein one, two, three or more amino acid residues may be substituted by a different amino acid; and/or
  (c) the heavy chain variable region of SEQ ID NO: 5, wherein one, two, three or more amino acid residues may be substituted by a different amino acid, and the light chain variable region of SEQ ID NO: 6, wherein one or more of these amino acids may be substituted by a different amino acid; and/or
  (d) the heavy chain CDR 1, 2 and 3 (HCDR1, HCDR2, HCDR3) amino acid sequences as shown in SEQ ID NOS: 7-9, 10-11 and 12, respectively, wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NOS: 13, 14 or 15, respectively, wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NOS: 7, 8 or 9, 10 or 11 and 12, respectively, wherein one, two, three or more amino acid residues of any CDR may be substituted by a different amino acid, and the light chain CDR 1, 2 and 3 (LCDR1, LCDR2, LCDR3) amino acid sequences as shown in SEQ ID NOS: 13, 14 or 15, wherein one, two, three or more amino acid residues may be substituted by a different amino acid; and/or (g) the heavy chain variable region which is at least 60%, 70%, 80%, 85%, 90% or 95% identical to the variable region having an amino acid sequence of SEQ ID NO: 5, wherein one, two, three or more amino acid residues may be substituted by a different amino acid; and/or (h) the light chain variable region which is at least 60%, 70%, 80%, 85%, 90% or 95% identical to the variable region having an amino acid sequence of SEQ ID NO: 6, wherein one, two, three or more amino acid residues may be substituted by a different amino acid.

Antibody 12B11

The amino acid sequence of the heavy chain variable region of antibody 12B11 is listed below:

```
                                          (SEQ ID NO: 16)
QLVQSGPELKNPGETVKISCKASGYTFTNYGMNWVKQAPGKGLKWMGWIN

TYTGEPTYADDFKGRFAFSLETSASTAYLQINNLKNEDTATYFCAHGPWL

AYWGQGTLVTVS.
```

The amino acid sequence of the light chain variable region of antibody 12B11 is listed below:

```
                                          (SEQ ID NO: 17)
DIKMTQSPSSMYASLGERVTITCKASQDINVYLSWFQQKPGKSPKTLIYR

AIRLVDGVPSRFSGSGSGQDYSLTISSLDYEDMGIYYCLQYDELPYTFGG

GTKLEIE.
```

In one aspect, a purified polypeptide is provided which encodes an antibody, wherein the antibody comprises: an HCDR1 region comprising an amino acid sequence GYTFTNYGMN as set forth in SEQ ID NO: 20, or a sequence of at least 4, 5, 6, 7, 8, 9 or 10 contiguous amino acids thereof (e.g., NYGMN (SEQ ID NO: 18), GYTFTN (SEQ ID NO: 19)), wherein one or more of these amino acids may be substituted by a different amino acid; an HCDR2 region comprising an amino acid sequence WINTYTGEPTYADDFKG as set forth in SEQ ID NO: 21, or a sequence of at least 4, 5, 6, 7, 8, 9 or 10 contiguous amino acids thereof (e.g., WINTYTGEPT (SEQ ID NO: 22)), wherein one or more of these amino acids may be substituted by a different amino acid; an HCDR3 region comprising an amino acid sequence GPWLAY as set forth in SEQ ID NO: 23, or a sequence of at least 4, 5, 6, 7, 8, 9 or 10 contiguous amino acids thereof, wherein one or more of these amino acids may be substituted by a different amino acid; an LCDR1 region comprising an amino acid sequence KASQDINVYLS as set forth in SEQ ID NO: 24, or a sequence of at least 4, 5, 6, 7, 8, 9 or 10 contiguous amino acids thereof, wherein one or more of these amino acids may be substituted by a different amino acid; an LCDR2 region comprising an amino acid sequence RAIRLVD as set forth in SEQ ID NO: 25, or a sequence of at least 4, 5, 6, 7, 8, 9 or 10 contiguous amino acids thereof, wherein one or more of these amino acids may be substituted by a different amino acid; and/or an LCDR3 region comprising an amino acid sequence LQYDELPYT as set forth in SEQ ID NO: 26, or a sequence of at least 4, 5, 6, 7, 8, 9 or 10 contiguous amino acids thereof, wherein one or more of these amino acids may be deleted or substituted by a different amino acid.

In another aspect, an antibody is provided that binds human KIR3DL2, comprising:

(a) the heavy chain variable region of SEQ ID NO: 16, wherein one, two, three or more amino acid residues may be substituted by a different amino acid; and/or (b) the light chain variable region of SEQ ID NO: 17, wherein one, two, three or more amino acid residues may be substituted by a different amino acid; and/or (c) the heavy chain variable region of SEQ ID NO: 16, wherein one or more amino acid residues may be substituted by a different amino acid, and the light chain variable region of SEQ ID NO: 17, wherein one, two, three or more of these amino acids may be substituted by a different amino acid; and/or (d) the heavy chain CDR 1, 2 and 3 (HCDR1, HCDR2, HCDR3) amino acid sequences as shown in SEQ ID NOS: 18, 19 or 20, 21 or 22 and 23, respectively, wherein one, two, three or more amino acid residues of any CDR may be substituted by a different amino acid; and/or (e) the light chain CDR 1, 2 and 3 (LCDR1, LCDR2, LCDR3) amino acid sequences as shown in SEQ ID NOS: 24, 25 and 26, wherein one, two, three or more amino acid residues of any CDR may be substituted by a different amino acid; and/or (f) the heavy chain CDR 1, 2 and 3 (HCDR1, HCDR2, HCDR3) amino acid sequences as shown in SEQ ID NOS: 18, 19 or 20, 21 or 22 and 23, respectively, wherein one or more amino acid residues of any CDR may be substituted by a different amino acid, and the light chain CDR 1, 2 and 3 (LCDR1, LCDR2, LCDR3) amino acid sequences as shown in SEQ ID NOS: 24, 25 and 26, wherein one, two, three or more amino acid residues of any CDR may be substituted by a different amino acid; and/or (g) the heavy chain variable region which is at least 60%, 70%, 80%, 85%, 90% or 95% identical to the variable region having an amino acid sequence of SEQ ID NO: 16, wherein one, two, three or more amino acid residues may be substituted by a different amino acid; and/or (h) the light chain variable region which is at least 60%, 70%, 80%, 85%, 90% or 95% identical to the variable region having an amino acid sequence of SEQ ID NO: 17, wherein one, two, three or more amino acid residues may be substituted by a different amino acid.

Antibody 2B12

The amino acid sequence of the heavy chain variable region of antibody 2B12 is listed below (Kabat definition CDRs underlined):

```
                                          (SEQ ID NO: 32)
Q I Q L V Q S G P E L K K P G E T V R I S C K A S
```

-continued

```
G Y T F T T A G M Q W V Q K T P G K G L K W I G W

I N S H S G V P K Y A E D F K G R F A F S L E T S

A S T A Y L Q I S T L K N E D T A T Y F C A R G G

D E G V M D Y W G Q G T S V T V S.
```

The amino acid sequence of the light chain variable region of antibody 2B12 is listed below (CDRs underlined):

```
                                          (SEQ ID NO: 33)
D I V M T Q S H K F M S T S L G D R V S F T C K A

S Q D V S T A V A W Y Q Q K P G Q S P K L L I Y W

T S T R H T G V P D R F T G S G S G T D Y T L T I

S S V Q A E D L A L Y Y C Q Q H Y S T P W T F G G

G T K L E I K.
```

In one aspect, a purified polypeptide is provided which encodes an antibody, wherein the antibody comprises: an HCDR1 region comprising an amino acid sequence GYTFT-TAGMQ as set forth in SEQ ID NO: 36, or a sequence of at least 4, 5, 6, 7, 8, 9 or 10 contiguous amino acids thereof (e.g., GYTFTT (SEQ ID NO: 34) or TAGMQ (SEQ ID NO: 35)), wherein one or more of these amino acids may be substituted by a different amino acid; an HCDR2 region comprising an amino acid sequence WINSHSGVPKYAE-DFK as set forth in SEQ ID NO: 37, or a sequence of at least 4, 5, 6, 7, 8, 9 or 10 contiguous amino acids thereof (e.g., WINSHSGVP (SEQ ID NO: 38)), wherein one or more of these amino acids may be substituted by a different amino acid; an HCDR3 region comprising an amino acid sequence GGDEGVMDYW as set forth in SEQ ID NO: 39, or a sequence of at least 4, 5, 6, 7, 8, 9 or 10 contiguous amino acids thereof, wherein one or more of these amino acids may be substituted by a different amino acid; an LCDR1 region comprising an amino acid sequence KASQDVSTAVA as set forth in SEQ ID NO: 40, or a sequence of at least 4, 5, 6, 7, 8, 9 or 10 contiguous amino acids thereof, wherein one or more of these amino acids may be substituted by a different amino acid; an LCDR2 region comprising an amino acid sequence WTSTRHT as set forth in SEQ ID NO: 41, or a sequence of at least 4, 5, 6, 7, 8, 9 or 10 contiguous amino acids thereof, wherein one or more of these amino acids may be substituted by a different amino acid; and/or an LCDR3 region comprising an amino acid sequence QQHYSTPWT as set forth in SEQ ID NO: 42, or a sequence of at least 4, 5, 6, 7, 8, 9 or 10 contiguous amino acids thereof, wherein one or more of these amino acids may be deleted or substituted by a different amino acid.

In another aspect, an antibody is provided that binds human KIR3DL2, comprising:
 (a) the heavy chain variable region of SEQ ID NO: 32, wherein one, two, three or more amino acid residues may be substituted by a different amino acid; and/or
 (b) the light chain variable region of SEQ ID NO: 33, wherein one, two, three or more amino acid residues may be substituted by a different amino acid; and/or
 (c) the heavy chain variable region of SEQ ID NO: 32, wherein one or more amino acid residues may be substituted by a different amino acid, and the light chain variable region of SEQ ID NO: 33, wherein one, two, three or more of these amino acids may be substituted by a different amino acid; and/or
 (d) the heavy chain CDR 1, 2 and 3 (HCDR1, HCDR2, HCDR3) amino acid sequences as shown in SEQ ID NOS: 34, 35 or 36, 37 or 38 and 39, respectively, wherein one, two, three or more amino acid residues of any CDR may be substituted by a different amino acid; and/or
 (e) the light chain CDR 1, 2 and 3 (LCDR1, LCDR2, LCDR3) amino acid sequences as shown in SEQ ID NOS: 40, 41 and 42, wherein one, two, three or more amino acid residues of any CDR may be substituted by a different amino acid; and/or
 (f) the heavy chain CDR 1, 2 and 3 (HCDR1, HCDR2, HCDR3) amino acid sequences as shown in SEQ ID NOS: 34, 35 or 36, 37 or 38 and 39, respectively, wherein one or more amino acid residues of any CDR may be substituted by a different amino acid, and the light chain CDR 1, 2 and 3 (LCDR1, LCDR2, LCDR3) amino acid sequences as shown in SEQ ID NOS: 40, 41 and 42, wherein one, two, three or more amino acid residues of any CDR may be substituted by a different amino acid; and/or
 (g) the heavy chain variable region which is at least 60%, 70%, 80%, 85%, 90% or 95% identical to the variable region having an amino acid sequence of SEQ ID NO: 32, wherein one, two, three or more amino acid residues may be substituted by a different amino acid; and/or
 (h) the light chain variable region which is at least 60%, 70%, 80%, 85%, 90% or 95% identical to the variable region having an amino acid sequence of SEQ ID NO: 33, wherein one, two, three or more amino acid residues may be substituted by a different amino acid.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In another aspect, an antibody is provided that competes for KIR3DL2 binding with a monoclonal antibody of (a) to (h), for any of the above antibodies.

Antibody Epitopes

While it will be appreciated that any suitable antibody can be used, in one aspect the antibodies that are used bind substantially the same epitope as antibody 19H12 or 12B11. In another embodiment, the antibodies at least partially overlap, or include at least one residue in the segment corresponding to residues 1-192, residues 1-98, or residues 99-192 of the KIR3DL2 polypeptide of SEQ ID NO: 1 (or a subsequence thereof). In one embodiment, all key residues of the epitope are in a segment corresponding to residues 1-192, residues 1-98 or residues 99-192 of the KIR3DL2 polypeptide of SEQ ID NO: 1. In one embodiment, the antibodies bind an epitope comprising 1, 2, 3, 4, 5, 6, 7 or more residues in the segment corresponding to residues 1-192, 1-98 or 99-192 of the KIR3DL2 polypeptide of SEQ ID NO: 1. Preferably the residues bound by the antibody are present on the surface of the KIR3DL2 polypeptide.

Optionally, the antibodies bind an epitope comprising residue P179 and/or residue S181 of SEQ ID NO: 1. Optionally, the antibodies bind to an epitope comprising 1, 2, 3, 4, 5, 6 or 7 or more residues selected from the group consisting of N99, H100, E130, H131, F132, V178, P179, H180, S181, P182, Y183 and/or residue Q184 of SEQ ID NO: 1.

The Examples section herein describes the testing of a series of mutant human KIR3DL2 polypeptides. Binding of anti-KIR3DL2 antibody to cells transfected with the KIR3DL2 mutants was measured and compared to the ability of anti-KIR3DL2 antibody to bind wild-type KIR3DL2 polypeptide (SEQ ID NO: 1). A reduction in binding between an anti-KIR3DL2 antibody and a mutant KIR3DL2 polypeptide as used herein means that there is a reduction in binding affinity (e.g., as measured by known methods such FACS testing of cells expressing a particular mutant, or Biacore testing of binding to mutant polypeptides) and/or a reduction in the total binding capacity of the anti-KIR3DL2 antibody (e.g., as evidenced by a decrease in Bmax in a plot of anti-KIR3DL2 antibody concentration versus polypeptide concentration). A significant reduction in binding indicates that the mutated residue is directly involved in binding to the anti-KIR3DL2 antibody or is in close proximity to the binding protein when the anti-KIR3DL2 antibody is bound to KIR3DL2. An antibody epitope may thus include such residue and may include additional residues spatially adjacent to such residue.

In some embodiments, a significant reduction in binding means that the binding affinity and/or capacity between an anti-KIR3DL2 antibody and a mutant KIR3DL2 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild-type KIR3DL2 polypeptide (e.g., the polypeptide shown in SEQ ID NO: 1). In certain embodiments, binding is reduced below detectable limits. In some embodiments, a significant reduction in binding is evidenced when binding of an anti-KIR3DL2 antibody to a mutant KIR3DL2 polypeptide is less than 50% (e.g., less than 45%, 40%, 35%, 30%, 25%, 20%, 15% or 10%) of the binding observed between the anti-KIR3DL2 antibody and a wild-type KIR3DL2 polypeptide (e.g., the extracellular domain shown in SEQ ID NO: 1). Such binding measurements can be made using a variety of binding assays known in the art. A specific example of one such assay is described in the Examples section.

In some embodiments, anti-KIR3DL2 antibodies are provided that exhibit significantly lower binding for a mutant KIR3DL2 polypeptide in which a residue in a wild-type KIR3DL2 polypeptide (e.g., SEQ ID NO: 1) is substituted. In the shorthand notation used here, the format is: Wild type residue: Position in polypeptide: Mutant residue, with the numbering of the residues as indicated in SEQ ID NO: 1.

Optionally, the antibodies have reduced binding to a KIR3DL2 polypeptide having a substitution at residues N99, H100, E130, H131, F132, V178, P179, H180, S181, P182, Y183 and/or Q184 of SEQ ID NO: 1.

In some embodiments, an anti-KIR3DL2 antibody binds a wild-type KIR3DL2 polypeptide having a sequence of SEQ ID NO: 1 but has decreased binding to a mutant KIR3DL2 polypeptide having any one or more (e.g., 1, 2, 3 or 4) of the following mutations: P179T and/or S181T (with reference to SEQ ID NO: 1). In one embodiment, binding to the mutant KIR3DL2 is significantly reduced compared to binding to the wild-type KIR3DL2.

In some embodiments, anti-KIR3DL2 antibodies are provided that exhibit significantly lower binding for a mutant KIR3DL2 polypeptide in which a residue in a segment corresponding to residues 1-98, residues 99-292, or residues 99-192 (or a subsequence thereof) in a wild-type KIR3DL2 polypeptide (e.g., SEQ ID NO: 1) is substituted with a different amino acid.

In one aspect, an antibody can compete with monoclonal antibody AZ158, 19H12, 2B12 or 12B11 and recognize binding to, or have immunospecificity for substantially or essentially the same, or the same, epitope or "epitopic site" on a KIR3DL2 molecule as, monoclonal antibody AZ158, 19H12, 2B12 or 12B11. In other embodiments, the monoclonal antibody consists of, or is a derivative or fragment of, antibody AZ158, 19H12, 2B12 or 12B11.

It will be appreciated that, while antibodies may bind to the same epitope as antibody AZ158, 19H12, 2B12 or 12B11, suitable antibodies can recognize and be raised against any part of the KIR3DL2 polypeptide so long as the antibody binds KIR3DL2 and has the desired functionality. For example, any fragment of KIR3DL2, e.g., human KIR3DL2, or any combination of KIR3DL2 fragments, can be used as immunogens to raise antibodies, and the antibodies can recognize epitopes at any location within the KIR3DL2 polypeptide, so long as they can do so on KIR3DL2-expressing NK cells as described herein. In an embodiment, the recognized epitopes are present on the cell surface, i.e., they are accessible to antibodies present outside of the cell. Optionally, the epitope is the epitope specifically recognized by antibody AZ158, 19H12, 2B12 or 12B11. Further, antibodies recognizing distinct epitopes within KIR3DL2 can be used in combination, e.g., to bind to KIR3DL2 polypeptides with maximum efficacy and breadth among different individuals.

The antibodies may be produced by a variety of techniques known in the art. Typically, they are produced by immunization of a non-human animal, optionally a mouse, with an immunogen comprising a KIR3DL2 polypeptide, optionally a human KIR3DL2 polypeptide. The KIR3DL2 polypeptide may comprise the full-length sequence of a human KIR3DL2 polypeptide, or a fragment or derivative thereof, typically an immunogenic fragment, i.e., a portion of the polypeptide comprising an epitope exposed on the surface of cells expressing a KIR3DL2 polypeptide, optionally the epitope recognized by the AZ158, 19H12, 2B12 or 12B11 antibody. Such fragments typically contain at least about 7 consecutive amino acids of the mature polypeptide sequence, or at least about 10 consecutive amino acids thereof. Fragments typically are essentially derived from the extra-cellular domain of the receptor. In one embodiment, the immunogen comprises a wild-type human KIR3DL2 polypeptide in a lipid membrane, typically at the surface of a cell. In one embodiment, the immunogen comprises intact cells, particularly intact human cells, optionally treated or lysed. In another embodiment, the polypeptide is a recombinant KIR3DL2 polypeptide.

The step of immunizing a non-human mammal with an antigen may be carried out in any manner well-known in the art for stimulating the production of antibodies in a mouse (see, for example, E. Harlow and D. Lane, Antibodies: A Laboratory Manual, Cold Spring Harbor Laboratory Press, Cold Spring Harbor, NY (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well-known to those of skill in the art and are not limiting in any way. These parameters may be different for different immunogens, but are easily elucidated.

Similarly, the location and frequency of immunization sufficient to stimulate the production of antibodies is also well-known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein are isolated by well-known techniques. The serum may be affinity purified using any of the immunogens set forth above linked to a solid support so as to obtain antibodies that react with KIR3DL2 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For exemplary monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single-cell suspension. The cells are washed, centrifuged and resuspended in a buffer that lyses any red blood cells. The solution is again centrifuged and remaining lymphocytes in the pellet are finally resuspended in fresh buffer.

Once isolated and present in single-cell suspension, the lymphocytes can be fused to an immortal cell line. This is typically a mouse myeloma cell line, although many other immortal cell lines useful for creating hybridomas are known in the art. Murine myeloma lines include, but are not limited to, those derived from MOPC-21 and MPC-11 mouse tumors available from the Salk Institute Cell Distribution Center, San Diego, U.S.A., and X63 Ag8653 and SP-2 cells available from the American Type Culture Collection, Rockville, Maryland U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages can be from littermates of the non-human mammal used to isolate splenocytes and are typically primed with incomplete Freund's adjuvant or the like several days before plating the hybridomas. Fusion methods are described in Goding, Monoclonal Antibodies: Principles and Practice, pp. 59-103 (Academic Press, 1986), the disclosure of which is herein incorporated by reference.

The cells are allowed to grow in the selection media for a sufficient time for colony formation and antibody production. This is usually between about 7 and about 14 days.

The hybridoma colonies are then assayed for the production of antibodies that specifically bind to KIR3DL2 polypeptide gene products, optionally the epitope specifically recognized by antibody AZ158, 19H12, 2B12 or 12B11. The assay is typically a colorimetric ELISA-type assay, although any assay may be employed that can be adapted to the wells that the hybridomas are grown in. Other assays include radioimmunoassays or fluorescence-activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to KIR3DL2 polypeptides, e.g., KIR3DL2-expressing cells.

Hybridomas that are confirmed to produce a monoclonal antibody can be grown in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing the monoclonal antibody (or the ascites fluid) is separated from the cells and the monoclonal antibody present therein is purified. Purification is typically achieved by gel electrophoresis, dialysis, chromatography using protein A or protein G Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in Ward et al., Nature, 341 (1989), p. 544, the entire disclosure of which is herein incorporated by reference.

The identification of one or more antibodies that bind(s) to KIR3DL2, particularly substantially or essentially the same epitope as monoclonal antibody AZ158, 19H12, 2B12 or 12B11, can be readily determined using any one of a variety of immunological screening assays in which antibody competition can be assessed. Many such assays are routinely practiced and are well-known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (AZ158, 19H12, 2B12 or 12B11, for example) and test antibodies are admixed (or pre-adsorbed) and applied to a sample containing KIR3DL2 polypeptides. Protocols based upon Western blotting and the use of BIACORE analysis are suitable for use in such competition studies.

In certain embodiments, one pre-mixes the control antibodies (AZ158, 19H12, 2B12 or 12B11, for example) with varying amounts of the test antibodies (e.g., about 1:10 or about 1:100) for a period of time prior to applying to the KIR3DL2 antigen sample. In other embodiments, the control and varying amounts of test antibodies can simply be admixed during exposure to the KIR3DL2 antigen sample. As long as one can distinguish bound from free antibodies (e.g., by using separation or washing techniques to eliminate unbound antibodies) and AZ158, 19H12, 2B12 or 12B11 from the test antibodies (e.g., by using species-specific or isotype-specific secondary antibodies or by specifically labeling AZ158, 19H12, 2B12 or 12B11 with a detectable label) one can determine if the test antibodies reduce the binding of AZ158, 19H12, 2B12 or 12B11 to the antigens, indicating that the test antibody recognizes substantially the same epitope as AZ158, 19H12, 2B12 or 12B11. The binding of the (labeled) control antibodies in the absence of a completely irrelevant antibody can serve as the control high value. The control low value can be obtained by incubating the labeled (AZ158, 19H12, 2B12 or 12B11) antibodies with unlabeled antibodies of exactly the same type (AZ158, 19H12, 2B12 or 12B11), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" or competes with the labeled (AZ158, 19H12, 2B12 or 12B11) antibody. Any test antibody that reduces the binding of AZ158, 19H12, 2B12 or 12B11 to KIR3DL2 antigens by at least about 50%, such as at least about 60%, or more preferably at least about 80% or 90% (e.g., about 65-100%), at any ratio of AZ158, 19H12, 2B12 or 12B11:test antibody between about 1:10 and about 1:100 is considered to be an antibody that binds to substantially the same epitope or determinant as AZ158, 19H12, 2B12 or 12B11. For example such test antibody will reduce the binding of AZ158, 19H12, 2B12 or 12B11 to the KIR3DL2 antigen by at least about 90% (e.g., about 95%).

Competition can also be assessed by, for example, a flow cytometry test. In such a test, cells bearing a given KIR3DL2 polypeptide can be incubated first with AZ158, 19H12, 2B12 or 12B11, for example, and then with the test antibody labeled with a fluorochrome or biotin. The antibody is said to compete with AZ158, 19H12, 2B12 or 12B11 if the binding obtained upon preincubation with a saturating amount of AZ158, 19H12, 2B12 or 12B11 is about 80%, about 50%, about 40% or less (e.g., about 30%, 20% or 10%) of the binding (as measured by means of fluorescence) obtained by the antibody without pre-incubation with AZ158, 19H12, 2B12 or 12B11. Alternatively, an antibody is said to compete with AZ158, 19H12, 2B12 or 12B11 if the binding obtained with a labeled AZ158, 19H12, 2B12 or 12B11 antibody (by a fluorochrome or biotin) on cells preincubated with a saturating amount of test antibody is about 80%, about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a KIR3DL2 antigen is immobilized may also be employed. The surface in the simple competition assay is for example a BIACORE chip (or other media suitable for surface plasmon resonance analysis). The control antibody (e.g., AZ158, 19H12, 2B12 or 12B11) is then brought into contact with the surface at a KIR3DL2-saturating concentration and the KIR3DL2 and surface binding of the control antibody is measured. This binding of the control antibody is compared with the binding of the control antibody to the KIR3DL2-containing surface in the absence of test antibody. In a test assay, a significant reduction in binding of the KIR3DL2-containing surface by the control antibody in the presence of a test antibody indicates that the test antibody recognizes substantially the same epitope as the control antibody such that the test antibody "cross-reacts" with the control antibody. Any test antibody that reduces the binding of control (such as AZ158, 19H12, 2B12 or 12B11) antibody to a KIR3DL2 antigen by at least about 30% or more, or about 40%, can be considered to be an antibody that binds to substantially the same epitope or determinant as a control (e.g., AZ158, 19H12, 2B12 or 12B11). For example, such a test antibody will reduce the binding of the control antibody (e.g., AZ158, 19H12, 2B12 or 12B11) to the KIR3DL2 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. For example, the antibody having higher affinity for the KIR3DL2 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Determination of whether an antibody binds within an epitope region can be carried out in ways known to the person skilled in the art. As one example of such mapping/characterization methods, an epitope region for an anti-KIR3DL2 antibody may be determined by epitope "footprinting" using chemical modification of the exposed amines/carboxyls in the KIR3DL2 protein. One specific example of such a footprinting technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring, H., Analytical Biochemistry, Vol. 267 (2) pp. 252-259 (1999); Engen, J. R. and Smith, D. L. (Anal. Chem. 73, 256A-265A (2001). Another example of a suitable epitope identification technique is nuclear magnetic resonance epitope mapping (NMR), where typically the position of the signals in two-dimensional NMR spectra of the free antigen and the antigen complexed with the antigen-binding peptide, such as an antibody, are compared. The antigen is typically selectively isotopically labeled with 15N so that only signals corresponding to the antigen and no signals from the antigen-binding peptide are seen in the NMR spectrum. Antigen signals originating from amino acids involved in the interaction with the antigen-binding peptide will typically shift position in the spectrum of the complex compared to the spectrum of the free antigen, and the amino acids involved in the binding can be identified that way. See, e.g., Ernst Schering Res. Found. Workshop, 44:149-67 (2004); Huang et al., Journal of Molecular Biology, 281(1):61-67 (1998); and Saito and Patterson, Methods, 1996 June, 9(3):516-24.

Epitope mapping/characterization also can be performed using mass spectrometry methods. See, e.g., Downard, J. Mass. Spectrom, 2000 April, 35(4):493-503 and Kiselar and Downard, Anal. Chem., 1999 May 1, 71(9):1792-801. Protease digestion techniques can also be useful in the context of epitope mapping and identification. Antigenic determinant-relevant regions/sequences can be determined by protease digestion, e.g., by using trypsin in a ratio of about 1:50 to KIR3DL2 or o/n digestion at pH 7-8, followed by mass spectrometry (MS) analysis for peptide identification. The peptides protected from trypsin cleavage by the anti-KIR3DL2 binder can subsequently be identified by comparison of samples subjected to trypsin digestion and samples incubated with antibody and then subjected to digestion by, e.g., trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the KIR3DL2 polypeptide that is not surface exposed and, accordingly, most likely not relevant in terms of immunogenicity/antigenicity. See, e.g., Manca, Ann 1st Super Sanita, 1991, 27:15-9 for a discussion of similar techniques.

Site-directed mutagenesis is another technique useful for elucidation of a binding epitope. For example, in "alanine-scanning", each residue within a protein segment is replaced with an alanine residue, and the consequences for binding affinity are measured. If the mutation leads to a significant reduction in binding affinity, it is most likely involved in binding. Monoclonal antibodies specific for structural epitopes (i.e., antibodies which do not bind the unfolded protein) can be used to verify that the alanine replacement does not influence the overall fold of the protein. See, e.g., Clackson and Wells, Science 1995, 267:383-386, and Wells, Proc Natl Acad Sci USA 1996, 93:1-6.

Electron microscopy can also be used for epitope "footprinting". For example, Wang et al., Nature 1992, 355:275-278 used coordinated application of cryoelectron microscopy, three-dimensional image reconstruction, and X-ray crystallography to determine the physical footprint of a Fab fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fagerstam et al., Journal of Molecular Recognition 1990, 3:208-14; Nice et al., J. Chromatogr. 1993, 646:159-168; Leipert et al., Angew. Chem. Int. Ed. 1998, 37:3308-3311; Kröger et al., Biosensors and Bioelectronics 2002, 17:937-944.

It should also be noted that an antibody binding the same or substantially the same epitope as an antibody can be identified in one or more of the exemplary competition assays described herein.

Once antibodies are identified that are capable of binding KIR3DL2 and/or having other desired properties, they will also typically be assessed, using standard methods including those described herein, for their ability to bind to other polypeptides, including unrelated polypeptides. Ideally, the antibodies only bind with substantial affinity to KIR3DL2, e.g., human KIR3DL2, and do not bind at a significant level to unrelated polypeptides. However, it will be appreciated that, as long as the affinity for KIR3DL2 is substantially greater (e.g., 5×, 10×, 50×, 100×, 500×, 1000×, 10,000×, or more) than it is for other, unrelated polypeptides, the antibodies are suitable for use in the present methods.

The binding of the antibodies to KIR3DL2-expressing cells can also be assessed in non-human primates, e.g., cynomolgus monkeys, or other mammals such as mice. Provided is an antibody, as well as fragments and derivatives thereof, wherein said antibody, fragment or derivative specifically binds KIR3DL2, and which furthermore binds KIR3DL2 from non-human primates, e.g., cynomolgus monkeys.

Upon immunization and production of antibodies in a vertebrate or cell, particular selection steps may be performed to isolate antibodies as claimed. In this regard, in a specific embodiment, the disclosure also relates to methods of producing such antibodies, comprising: (a) immunizing a non-human mammal with an immunogen comprising a KIR3DL2 polypeptide; (b) preparing antibodies from said immunized animal; and (c) selecting antibodies from step (b) that are capable of binding KIR3DL2.

In one aspect of any of the embodiments, the antibodies prepared according to the present methods are monoclonal antibodies. In another aspect, the non-human animal used to produce antibodies is a mammal, such as a rodent, bovine, porcine, fowl, horse, rabbit, goat, or sheep.

According to an alternate embodiment, the DNA encoding an antibody that binds an epitope present on KIR3DL2 polypeptides is isolated from the hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding a monoclonal antibody, e.g., antibody 19H12, 2B12 or 12B11, can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells, such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen-binding site in order to optimize the binding specificity of the antibody.

Recombinant expression in bacteria of DNA encoding the antibody is well-known in the art (see, for example, Skerra et al., Curr. Opinion in Immunol., 5, pp. 256 (1993), and Pluckthun, Immunol. 130, p. 151 (1992)).

Once an antigen-binding compound is obtained it may be assessed for its ability to induce ADCC or CDC towards, inhibit the activity and/or proliferation of and/or cause the elimination of KIR3DL2-expressing target cells. Assessing the antigen-binding compound's ability to induce ADCC or CDC (complement-dependent cytotoxicity) or generally lead to the elimination or inhibition of activity of KIR3DL2-expressing target cells can be carried out at any suitable stage of the method. This assessment can be useful at one or more of the various steps involved in the identification, production and/or development of an antibody (or other compound) destined for therapeutic use. For example, activity may be assessed in the context of a screening method to identify candidate antigen-binding compounds, or in methods where an antigen-binding compound is selected and made human suitable (e.g., made chimeric or humanized in the case of an antibody), where a cell expressing the antigen-binding compound (e.g., a host cell expressing a recombinant antigen-binding compound) has been obtained and is assessed for its ability to produce functional antibodies (or other compounds), and/or where a quantity of antigen-binding compound has been produced and is to be assessed for activity (e.g., to test batches or lots of product). Generally the antigen-binding compound will be known to specifically bind to a KIR3DL2 polypeptide. The step may involve testing a plurality (e.g., a very large number using high-throughput screening methods or a smaller number) of antigen-binding compounds.

Testing CDC and ADCC can be carried out by various assays including those known in the art and those described in the experimental examples herein. Testing ADCC typically involves assessing cell-mediated cytotoxicity in which a KIR3DL2-expressing target cell (e.g., a PTCL cell or other KIR3DL2-expressing cell) with bound anti-KIR3DL2 antibody is recognized by an effector cell bearing Fc receptors, without the involvement of complement. A cell which does not express a KIR3DL2 antigen can optionally be used as a control. Activation of NK cell cytotoxicity is assessed by measuring an increase in cytokine production (e.g., IFN-γ production) or cytotoxicity markers (e.g., CD107 mobilization). In one embodiment, the antibody will induce an increase in cytokine production, expression of cytotoxicity markers, or target cell lysis of at least 20%, 50%, 80%, 100%, 200% or 500% in the presence of target cells, compared to a control antibody (e.g., an antibody not binding to KIR3DL2, a KIR3DL2 antibody having murine constant regions). In another example, lysis of target cells is detected, e.g., in a chromium release assay; for example the antibody will induce lysis of at least 10%, 20%, 30%, 40% or 50% of the target cells.

Fragments and derivatives of antibodies (which are encompassed by the term "antibody" or "antibodies" as used in this application, unless otherwise stated or clearly contradicted by context) can be produced by techniques that are known in the art. "Fragments" comprise a portion of the intact antibody, generally the antigen-binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single-chain polypeptide"), including without limitation (1) single-chain Fv molecules, (2) single-chain polypeptides containing only one light chain variable domain, or a fragment thereof that contains the three CDRs of the light chain variable domain, without an associated heavy chain moiety and (3) single-chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

In certain embodiments, the DNA of a hybridoma producing an antibody can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Thus, according to another embodiment, the antibody is humanized. "Humanized" forms of antibodies are specific chimeric immunoglobulins, immunoglobulin chains or fragments thereof (such as Fv, Fab, Fab', F(ab')2, or other antigen-binding subsequences of antibodies) which contain minimal sequences derived from the murine immunoglobulin. For the most part, humanized antibodies are human immunoglobulins (recipient antibody) in which residues from a complementarity-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al., Nature, 332, pp. 323 (1988); Presta, Curr. Op. Struct. Biol., 2, pp. 593 (1992); Verhoeyen et al., Science, 239, pp. 1534; and U.S. Pat. No. 4,816,567, the entire disclosures of which are herein incorporated by reference. Methods for humanizing the antibodies are well-known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for KIR3DL2 receptors and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Another method of making "humanized" monoclonal antibodies is to use a XenoMouse (Abgenix, Fremont, CA) as the mouse for immunization. A XenoMouse is a murine host that has had its immunoglobulin genes replaced by functional human immunoglobulin genes. Thus, antibodies produced by this mouse or in hybridomas made from the B cells of this mouse are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362:255 (1993)), or by selection of antibody repertoires using phage display methods. Such techniques are known to the skilled person and can be implemented starting from monoclonal antibodies as disclosed in the present application.

A KIR3DL2 binding compound, e.g., an anti-KIR3DL2 antibody, may be further bound to a second moiety, wherein the antibody is capable of delivering the second moiety to a KIR3DL2-expressing cell. Optionally the second moiety is a therapeutic agent, a toxic agent, and/or a detectable agent.

While antibodies in underivatized or unmodified form, particularly of the IgG1 or IgG3 type, are expected to inhibit the proliferation of the overproliferating cells or be cytotoxic towards overproliferating cells such as in those from a PTCL patient, e.g., by directing ADCC and/or CDC toward KIR3DL2-expressing PTCL cells, it is also possible to prepare derivatized antibody immunoconjugates that are cytotoxic. In one embodiment, once the KIR3DL2-specific antibodies are isolated and optionally otherwise modified (e.g., humanized), they will be derivatized to make them toxic to cells. In this way, administration of the antibody to PTCL patients will lead to the relatively specific binding of the antibody to overproliferating cells, thereby directly killing or inhibiting the cells underlying the disorder.

Any of a large number of toxic moieties or strategies can be used to produce such antibodies. In certain embodiments, the antibodies will be directly derivatized with radioisotopes or other toxic compounds. Examples of toxic agents used in immunoconjugates in development include taxanes, anthracyclines, camptothecins, epothilones, mitomycins, combretastatins, vinca alkaloids, nitrogen mustards, maytansinoids, calicheamycins, duocarmycins, tubulysins, dolastatins, auristatins, enediynes, pyrrolobenzodiazepines, ethylenimines, radioisotopes, therapeutic proteins and peptides, and toxins or fragments thereof. Any type of moiety with a cytotoxic or cytoinhibitory effect can be used in conjunction with the present antibodies to inhibit or kill specific NK receptor-expressing cells, including radioisotopes, toxic proteins, and toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, epidphyllotoxins, antimetabolites, alkylating agents, antibiotics, antimitotics, antiangiogenic and apoptotic agents, particularly doxorubicin, methotrexate, camptothecins, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, 5-fluorouridine, ribonuclease (RNase), DNase I, staphylococcal enterotoxin-A, pokeweed antiviral protein, gelonin, diphtherin toxin, and others (see, e.g., Remington's Pharmaceutical Sciences, 19th Ed. (Mack Publishing Co. 1995); Goodman and Gilman's The Pharmacological Basis of Therapeutics (McGraw-Hill, 2001); Pastan et al. (1986) Cell 47:641; Goldenberg (1994) Cancer Journal for Clinicians 44:43; and U.S. Pat. No. 6,077,499, the entire disclosures of which are herein incorporated by reference).

In one embodiment, the antibody will be derivatized with a radioactive isotope, such as 1-131. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. The radionuclide may have a decay energy in the range of 20 to 6,000 keV, optionally in the ranges of 60 to 200 keV for an Auger emitter, 100-2,500 keV for a beta emitter, and 4,000-6,000 keV for an alpha emitter. Also provided are radionuclides that substantially decay with generation of alpha particles.

In view of the ability of the anti-KIR3DL2 antibodies to induce ADCC and CDC, the antibodies can also be made with modifications that increase their ability to bind Fc receptors which can affect effector functions such as antibody-dependent cytotoxicity, mast cell degranulation, and phagocytosis, as well as immunomodulatory signals such as regulation of lymphocyte proliferation and antibody secretion. Typical modifications include modified human IgG1 constant regions comprising at least one amino acid modification (e.g., substitutions, deletions, insertions), and/or altered types of glycosylation, e.g., hypofucosylation. Such modifications can affect interaction with Fc receptors: FcγRI (CD64), FcγRII (CD32), and FcγRIII (CD16). FcγRI (CD64), FcγRIIA (CD32A) and FcγRIII (CD16) are activating (i.e., immune system-enhancing) receptors while FcγRIIB (CD32B) is an inhibiting (i.e., immune system-dampening) receptor. A modification may, for example, increase binding of the Fc domain to FcγRIIIa on effector (e.g., NK) cells.

Anti-KIR3DL2 antibodies may comprise an Fc domain (or portion thereof) of human IgG1 or IgG3 isotype, optionally modified. Residues 230-341 (Kabat EU) are the Fc CH2 region. Residues 342-447 (Kabat EU) are the Fc CH3 region. Anti-KIR3DL2 antibodies may comprise a variant Fc region having one or more amino acid modifications (e.g., substitutions, deletions, insertions) in one or more portions, which modifications increase the affinity and avidity of the variant Fc region for an FcγR (including activating and inhibitory FcγRs). In some embodiments, said one or more amino acid modifications increase the affinity of the variant Fc region for FcγRIIIA and/or FcγRIIA. In another embodiment, the variant Fc region further specifically binds FcγRIIB with a lower affinity than does the Fc region of the comparable parent antibody (i.e., an antibody having the same amino acid sequence as the antibody except for the one or more amino acid modifications in the Fc region). For example, one or both of the histidine residues at amino acid positions 310 and 435 may be substituted, for example by lysine, alanine, glycine, valine, leucine, isoleucine, proline, methionine, tryptophan, phenylalanine, serine or threonine (see, e.g., PCT publication no. WO 2007/080277); such substituted constant regions provide decreased binding to the inhibitory FcγRIIB without decreasing binding to the activatory FcγRIIIA In some embodiments, such modifications increase the affinity of the variant Fc region for FcγRIIIA and/or FcγRIIA and also enhance the affinity of the variant Fc region for FcγRIIB relative to the parent antibody. In other embodiments, said one or more amino acid modifications increase the affinity of the variant Fc region for FcγRIIIA and/or FcγRIIA but do not alter the affinity of the variant Fc regions for FcγRIIB relative to the Fc region of the parent antibody. In another embodiment, said one or more amino acid modifications enhance the affinity of the variant Fc region for FcγRIIIA and FcγRIIA but reduce the affinity for FcγRIIB relative to the parent antibody. Increased affinity and/or avidity results in detectable binding to the FcγR or FcγR-related activity in cells that express low levels of the FcγR when binding activity of the parent molecule (without the modified Fc region) cannot be detected in the cells.

The affinities and binding properties of the molecules for an FcγR can be determined using in vitro assays (biochemical or immunological-based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, and immunoprecipitation assay.

In some embodiments, the molecules comprising a variant Fc region comprise at least one amino acid modification (for example, possessing 1, 2, 3, 4, 5, 6, 7, 8, 9, or more amino acid modifications) in the CH3 domain of the Fc region. In other embodiments, the molecules comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, the molecules comprise at least two amino acid modifications (for example, possessing 2, 3, 4, 5, 6, 7, 8, 9, or more amino acid modifications), wherein at least one such modification is in the CH3 region and at least one such modification is in the CH2 region. Amino acid modifications may be made for example in the hinge region. In a particular embodiment, the invention encompasses amino acid modification in the CH1 domain of the Fc region, which is defined as extending from amino acids 216-230.

Any combination of Fc modifications can be made, for example any combination of different modifications disclosed in U.S. Pat. Nos. 7,632,497; 7,521,542; 7,425,619; 7,416,727; 7,371,826; 7,355,008; 7,335,742; 7,332,581; 7,183,387; 7,122,637; 6,821,505; and 6,737,056; in PCT Publication Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249; and WO 04/063351; and in Presta, L. G. et al. (2002) Biochem. Soc. Trans. 30(4):487-490; Shields, R. L. et al. (2002) J. Biol. Chem. 277(30):26733-26740; and Shields, R. L. et al. (2001) J. Biol. Chem. 276(9):6591-6604).

Anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 239, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 332, 333, 334, 335, 337, 338, 339, 340, 359, 360, 370, 373, 376, 378, 392, 396, 399, 402, 404, 416, 419, 421, 430, 434, 435, 437, 438 and/or 439.

Anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 329, 298, 330, 332, 333 and/or 334 (e.g., S239D, S298A, A330L, I332E, E333A and/or K334A substitutions).

In one embodiment, antibodies having variant or wild-type Fc regions may have altered glycosylation patterns that increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) J. Biol. Chem. 277:26733-26740; Umana et al. (1999) Nat. Biotech. 17:176-1; European Patent No. EP 1,176,195; and PCT Publication Nos. WO 06/133148, WO 03/035835, and WO 99/54342, each of which is incorporated herein by reference in its entirety.

Generally, such antibodies with altered glycosylation are "glyco-optimized" such that the antibody has a particular N-glycan structure that produces certain desirable properties, including, but not limited to, enhanced ADCC and effector cell receptor-binding activity when compared to non-modified antibodies or antibodies having a naturally occurring constant region and produced by murine myeloma NSO and Chinese Hamster Ovary (CHO) cells (Chu and Robinson, Current Opinion Biotechnol. 2001, 12: 180-7), HEK293T-expressed antibodies as produced herein in the Examples section, or other mammalian host cell lines commonly used to produce recombinant therapeutic antibodies.

Monoclonal antibodies produced in mammalian host cells contain an N-linked glycosylation site at Asn297 of each heavy chain. Glycans on antibodies are typically complex biantennary structures with very low or no bisecting N-acetylglucosamine (bisecting GlcNAc) and high levels of core fucosylation. Glycan termini contain very low or no terminal sialic acid and variable amounts of galactose. For a review of effects of glycosylation on antibody function, see, e.g., Wright & Morrison, Trends Biotechnol. 15:26-31 (1997). Considerable work shows that changes to the sugar composition of the antibody glycan structure can alter Fc effector functions. The important carbohydrate structures contributing to antibody activity are believed to be the fucose residues attached via alpha-1,6 linkage to the innermost N-acetylglucosamine (GlacNAc) residues of the Fc region N-linked oligosaccharides (Shields et al., 2002).

FcγR binding requires the presence of oligosaccharides covalently attached to the conserved Asn297 in the Fc region of human IgG1, IgG2 or IgG3 type. Non-fucosylated oligosaccharide structures have recently been associated with dramatically increased in vitro ADCC activity. "Asn297" means amino acid asparagine located at about position 297 in the Fc region; based on minor sequence variations of antibodies, Asn297 can also be located some amino acids (usually not more than +3 amino acids) upstream or downstream.

Historically, antibodies produced in CHO cells contain about 2 to 6% in the population that are nonfucosylated. YB2/0 (rat myeloma) and Lecl3 cell lines (a lectin mutant of the CHO line which has a deficient GDP-mannose 4,6-dehydratase leading to the deficiency of GDP-fucose or GDP sugar intermediates that are the substrate of alpha6-fucosyltransferase) have been reported to produce antibodies with 78 to 98% non-fucosylated species. In other examples, RNA interference (RNAi) or knock-out techniques can be employed to engineer cells to either decrease the FUT8 mRNA transcript levels or knock out gene expression entirely, and such antibodies have been reported to contain up to 70% non-fucosylated glycan.

An antibody that binds to KIR3DL2 may be glycosylated with a sugar chain at Asn297. In one embodiment, an antibody will comprise a constant region comprising at least one amino acid alteration in the Fc region that improves antibody binding to FcγRIIIa and/or ADCC.

In one aspect, the antibodies are hypofucosylated in their constant region. Such antibodies may comprise an amino acid alteration or may not comprise an amino acid alteration but be produced or treated under conditions so as to yield such hypofucosylation. In one aspect, an antibody composition comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g., complex, hybrid and high mannose structures) which lacks fucose. In one embodiment, an antibody composition is provided which is free of antibodies comprising a core carbohydrate structure having fucose. The core carbohydrate will preferably be a sugar chain at Asn297.

In one embodiment, an antibody composition, e.g., a composition comprising antibodies which bind to KIR3DL2, is glycosylated with a sugar chain at Asn297, wherein the antibodies are partially fucosylated. Partially fucosylated antibodies are characterized in that the proportion of anti-KIR3DL2 antibodies in the composition that lack fucose within the sugar chain at Asn297 is between 20% and 90%, between 20% and 80%, between 20% and 50%, 55%, 60%, 70% or 75%, between 35% and 50%, 55%, 60%, 70% or 75%, or between 45% and 50%, 55%, 60%, 70% or 75%. Optionally the antibody is of human IgG1 or IgG3 type.

The sugar chain can further show any characteristics (e.g., presence and proportion of complex, hybrid and high mannose structures), including the characteristics of N-linked glycans attached to Asn297 of an antibody from a human cell, or of an antibody recombinantly expressed in a rodent cell, murine cell (e.g., CHO cell) or avian cell.

In one embodiment, the antibody is expressed in a cell that is lacking in a fucosyltransferase enzyme such that the cell line produces proteins lacking fucose in their core carbohydrates. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their core carbohydrates. These cell lines were created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22, the disclosures of which are incorporated herein by reference). Other examples have included the use of antisense suppression, double-stranded RNA (dsRNA) interference, hairpin RNA (hpRNA) interference or intron-containing hairpin RNA (ihpRNA) interference to functionally disrupt the FUT8 gene. In one embodiment, the antibody is expressed in a cell line with a functionally disrupted FUT8 gene, which encodes a fucosyl transferase, such that antibodies expressed in such a cell line exhibit hypofucosylation by reducing or eliminating the alpha 1,6 bond-related enzyme.

In one embodiment, the antibody is expressed in cell lines engineered to express glycoprotein-modifying glycosyl transferases (e.g., beta(1,4)-N-acetylglucosaminyl-transferase III (GnTHI)) such that antibodies expressed in the engineered cell lines exhibit increased bisecting GlcNac structures, which results in increased ADCC activity of the antibodies (PCT Publication WO 99/54342 by Umana et al. and Umana et al. (1999) Nat. Biotech. 17:176-180, the disclosures of which are incorporated herein by reference).

In another embodiment, the antibody is expressed and the fucosyl residue(s) is cleaved using a fucosidase enzyme. For example, the fucosidase alpha-L-fucosidase removes fucosyl residues from antibodies (Tarentino et al. (1975) Biochem. 14:5516-5523). In other examples, a cell line producing an antibody can be treated with a glycosylation inhibitor; Zhou et al. (2008) Biotech. and Bioengin. 99:652-665 described treatment of CHO cells with the alpha-mannosidase I inhibitor kifunensine, resulting in the production of antibodies with non-fucosylated oligomannose-type N-glucans.

In one embodiment, the antibody is expressed in a cell line which naturally has a low enzyme activity for adding fucosyl to the N-acetylglucosamine that binds to the Fc region of the antibody or does not have the enzyme activity, for example the rat myeloma cell line YB2/0 (ATCC CRL 1662). Other examples of cell lines include a variant CHO cell line, Led 3 cells, with reduced ability to attach fucosyl to Asn(297)-linked carbohydrates, also resulting in hypofucosylation of antibodies expressed in that host cell (WO 03/035835 (Presta et al); and Shields, R. X. et al. (2002) J. Biol. Chem. 277:26733-26740, the disclosures of which are incorporated herein by reference). In another embodiment, the antibody is expressed in an avian cell, e.g., an EBx® cell (Vivalis, France), which naturally yields antibodies with low fucose content, e.g., WO2008/142124. Hypofucosylated glycans can also be produced in cell lines of plant origin, e.g., WO 07/084926A2 (Biolex Inc.), WO 08/006554 (Greenovation Biotech GmbH), the disclosures of which are incorporated herein by reference.

Antibody Formulations

Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The antibodies may be employed in a method of modulating, e.g., inhibiting, the activity of KIR3DL2-expressing cells in a patient. This method comprises the step of contacting said composition with said patient. Such method will be useful for both prophylaxis and therapeutic purposes.

For use in administration to a patient, the composition will be formulated for administration to the patient. The compositions may be administered orally, parenterally, by inhalation spray, topically, rectally, nasally, buccally, vaginally or via an implanted reservoir. The administration routes used herein includes subcutaneous, intravenous, intramuscular, intra-articular, intrasynovial, intrasternal, intrathecal, intrahepatic, intralesional and intracranial injection or infusion techniques.

Sterile injectable forms of the compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms, may also be used for the purposes of formulation.

Several monoclonal antibodies have been shown to be efficient in clinical situations, such as Rituxan™ (Rituximab), Herceptin™ (Trastuzumab) or Xolair™ (Omalizumab), and similar administration regimens (i.e., formulations, doses and/or administration protocols) may be used with the antibodies. For example, an antibody present in a pharmaceutical composition can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition may be between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition for injection (e.g., intramuscular, i.v.) could be prepared to contain sterile buffered water (e.g., 1 ml for intramuscular), and from about 1 ng to about 100 mg, e.g., about 50 ng to about 30 mg or more, e.g., about 5 mg to about 25 mg, of an anti-KIR3DL2 antibody.

According to another embodiment, the antibody compositions may further comprise another therapeutic agent, including agents normally utilized for the particular therapeutic purpose for which the antibody is being administered, notably for the treatment of a PTCL. The additional therapeutic agent will normally be present in the composition in amounts typically used for that agent in a monotherapy for the particular disease or condition being treated. Such therapeutic agents include, but are not limited to, anti-inflammation agents, steroids, immune system suppressors, antibiotics, antivirals and other antibodies and fragments thereof.

Diagnosis and Treatment of Malignancies

Provided are methods useful in the diagnosis, prognosis and monitoring of a peripheral T cell lymphoma in an individual. In one embodiment, the methods comprise determining the level of expression of a KIR3DL2 nucleic acid or polypeptide in a biological sample from a patient, e.g., in tumor cells found in a biological sample. In one embodiment, the methods comprise determining the level of expression of a KIR3DL2 nucleic acid or polypeptide in a biological sample and comparing the level to a reference level (e.g., a value, weak cell surface staining, etc.) corresponding to a healthy individual(s). A determination that a biological sample expresses a KIR3DL2 nucleic acid or polypeptide at a level that is increased compared to the reference level indicates that the patient has a peripheral T cell lymphoma. Optionally, detecting a KIR3DL2 polypeptide in a biological sample comprises detecting a KIR3DL2 polypeptide expressed on the surface of a lymphocyte.

In one embodiment, the methods comprise: (a) determining whether an individual has a peripheral T cell lymphoma; and (b) if the individual has a peripheral T cell lymphoma, determining whether the individual has peripheral T cell lymphoma cells that express a KIR3DL2 polypeptide.

Also provided is a method for the assessment of the development level of a PTCL (staging disease) permitting the evaluation of the proportion (e.g., percentage) of malignant PTCL cells present within a certain body compartment of a patient. According to this method, cells from a biological sample collected from said body compartment are brought into contact with an anti-KIR3DL2 antibody and tumor cells (e.g., the proportion of cells) expressing a KIR3DL2 polypeptide at their surface are measured. The cells may be, for example CD4+ cells or CD4-CD8+ cells. A finding that tumor cells express, or predominantly express, KIR3DL2 indicates that the PTCL is an aggressive or advanced PTCL (e.g., stage IV, or more generally beyond stage II).

Also provided is a method for PTCL diagnosis, comprising bringing cells from a biological sample from an individual into contact with an anti-KIR3DL2 antibody and measuring the proportion (e.g., percentage) of T cells expressing a KIR3DL2 polypeptide at their surface, and comparing such proportion to the average proportion (e.g., percentage) of T cells expressing a KIR3DL2 polypeptide at their surface observed in non-PTCL humans (e.g., in healthy humans), wherein a PTCL-positive diagnosis is made when said measured proportion is significantly higher than said average proportion.

Further provided are therapeutic methods for treating individuals having a PTCL, susceptible to a PTCL or having experienced a PTCL, wherein the treatment involves administering anti-KIR3DL2 antibodies, anti-KIR3DL2 antibody compositions, and/or related compositions to an individual having or susceptible to PTCL. In one embodiment, the PTCL is an aggressive or advanced PTCL (e.g., stage IV, or more generally beyond stage II). In one embodiment, the PTCL is a non-cutaneous PTCL. In one embodiment, the PTCL is an aggressive T cell lymphoma. In one embodiment, the patient has relapsing or refractory disease. In one embodiment, the patient has a poor prognosis for disease progression (e.g., poor prognosis for survival) or has a poor prognosis for response to a therapy, e.g., antibody therapy, anti-CD30 antibody therapy, chemotherapy, etc.

In one embodiment, the PTCL is an aggressive T-cell neoplasm. In one embodiment, the PTCL is aggressive non-cutaneous PTCL. In one embodiment, the PTCL is an aggressive cutaneous PTCL, optionally a primary cutaneous CD4+ small/medium T cell lymphoma or a primary CD8+ small/medium T cell lymphoma. PTCL and PTCL-NOS may be specified to be diseases other than cutaneous T cell lymphomas, Sézary Syndrome and mycosis fungoides, which are considered distinct pathologies.

In one embodiment, the PTCL is a nodal (e.g., primarily or predominantly nodal) PTCL. Predominantly nodal PTCLs include, inter alia, peripheral T-cell lymphomas, not otherwise specified (PTCL-NOS), anaplastic large cell lymphomas (ALCL) and angioimmunoblastic T-cell lymphomas (AITL). For example a PTCL may be an aggressive, non-cutaneous, predominantly nodal PTCL (the disease may additionally have extra-nodal presentation).

In one embodiment, the PTCL is an extranodal (e.g., primarily extranodal) PTCL. For example a PTCL may be an aggressive, non-cutaneous, extranodal PTCL.

In one embodiment, the PTCL is an adult T cell leukemia or lymphoma (ATL), e.g., an HTLV+ ATL.

In one embodiment, the PTCL is an extranodal NK/T cell lymphoma, nasal type. In one embodiment, the PTCL is an enteropathy-associated T cell lymphoma.

In one embodiment, the PTCL is a hepatosplenic T cell lymphoma, optionally a hepatosplenic αβ T cell lymphoma, optionally a hepatosplenic γδ T cell lymphoma.

In one embodiment, the PTCL is an anaplastic large cell lymphoma (ALCL), optionally an ALK+ ALCL, optionally an ALK− ALCL. ALK+ ALCL generally enjoys favorable prognostics using conventional therapy (93% 5-year survival) but ALK− ALCL has poor prognostics (37%). ALCL is generally characterized by uniform CD30 surface expression. Anti-KIR3DL2 antibodies can therefore be used in combination with anti-CD30 antibodies (e.g., Adcetris™ (brentuximab vedotin, Seattle Genetics, Inc.)) for the treatment of ALCL. ALCL is generally also CD4+, although with occasional CD4− CD8+ cases. Anti-KIR3DL2 antibodies can therefore be used in combination with anti-CD4 antibodies to treat ALCL.

In one embodiment, the PTCL is an angioimmunoblastic T-cell lymphoma (AITL), optionally a cutaneous AITL, optionally a primary cutaneous CD4+ small/medium T cell lymphoma or a primary CD8+ small/medium T cell lymphoma, optionally a non-cutaneous AITL.

In one embodiment, the PTCL is an intestinal lymphoma, e.g., an intestinal ALCL.

In one embodiment, the PTCL is a T-cell prolymphocytic leukemia.

In one embodiment, a PTCL is a PTCL-NOS (peripheral T-cell lymphoma, not otherwise specified). PTCL-NOS, also referred to as PTCL-U or PTCL-unspecified, are aggressive lymphomas, mainly of nodal type, but extranodal involvement is common. The majority of nodal cases are CD4+ and CD8−, and CD30 can be expressed in large cell variants. Most patients with PTCL-NOS present with nodal involvement; however, a number of extranodal sites may also be involved (e.g., liver, bone marrow, gastrointestinal, skin). Studies generally report 5-year overall survival of approximately 30%-35% using standard chemotherapy. In the past, a number of definite entities corresponding to recognizable subtypes of T-cell neoplasm, such as Lennert lymphoma, T-zone lymphoma, pleomorphic T-cell lymphoma and T-immunoblastic lymphoma, have been described, but evidence that these correspond to distinctive clinicopathological entities is still lacking. For this reason the recent World Health Organization (WHO) classification of the hematopoietic and lymphoid neoplasms has collected these under the single broad category of PTCL-NOS/U. PTCL-NOS may therefore be specified to exclude certain distinctive clinicopathological entities such as T-cell prolymphocytic leukemia, ATL/adult T cell leukemia, extranodal NK/T cell leukemia (nasal type), EATL/enteropathy-type T cell lymphoma, hepatosplenic T cell lymphoma, subcutaneous panniculitis-like T cell lymphoma, ALCL/anaplastic large-cell lymphoma, and/or AITL/angioimmunoblastic T cell lymphoma. Anti-KIR3DL2 antibodies can be used in combination with anti-CD4 antibodies to treat PTCL-NOS. Anti-KIR3DL2 antibodies can be used in combination with anti-CD30 antibodies to treat PTCL-NOS that are CD30+.

PTCL diagnosis criteria can be those of standard medical guidelines, for example, according to the World Health Organization (WHO) classification system (see, e.g., World Health Organization. WHO Classification of Tumours of Haematopoietic and Lymphoid Tissues, 4$^{th}$ ed., Lyon, France: IARC Press, 2008). See also, e.g., Foss et al. (2011) Blood 117:6756-6767, the disclosures of which are incorporated herein by reference.

In one exemplary aspect, a method is provided of reducing progression of PTCL in a mammalian host (e.g., a human patient) having a detectable level of cancer cells, comprising administering an anti-KIR3DL2 antibody, an anti-KIR3DL2 antibody composition, or a related composition (e.g., a nucleic acid encoding an anti-KIR3DL2 antibody) in an amount sufficient to detectably reduce the progression of the hematological malignancies in the host.

In one exemplary aspect, a method is provided of treating PTCL in an individual having a poor disease prognosis and/or who has relapsed, is resistant or is not responsive to therapy with a first therapeutic agent.

Disease or cancer diagnosis and progression can be defined by standard criteria for the particular type of disease. PTCL (e.g., PTCL-NOS) is typically based on examination of peripheral blood or tissue biopsy for histological features supplemented by detailed immunohistochemistry, flow cytometry, cytogenetics and molecular genetics. Examination may include, for example, full blood count and differential, tests of renal and hepatic function, lactate dehydrogenase (LDH), Beta2 microglobulin, albumin, serum calcium, uric acid, bone marrow biopsy, chest X-ray and computerized tomography (CT) scan of chest, abdomen and pelvis. Progression is optionally determined by assessing the selective clonal expansion of initiated cells. Methods for detecting cancers and cancer progression can be achieved by any suitable technique, several examples of which are known in the art. Examples of suitable techniques include PCR and RT-PCR (e.g., of cancer cell-associated genes or "markers"), biopsy, imaging techniques, karyotyping and other chromosomal analysis, immunoassay/immunocytochemical detection techniques, histological and/or histopathology assays, cell kinetic studies and cell cycle analysis, flow cytometry, and physical examination techniques (e.g., for physical symptoms).

In one embodiment, diagnosing or assessing PTCL (e.g., PTCL-NOS) comprises chromosomal analysis. Cases of PTCL-NOS often show heterogeneous, variable morphology, with losses having been reported in 3q, 6q, 9p, 10q, 12q and/or 5q, and recurrent chromosomal gains, including in 8q, 9p and/or 19q. One CGH study in PTCL-NOS has shown frequent gains of 7q22-31, 1q, 3p, 5p and 8q24qter and losses of 6q22-24 and 10p13pter, and cases with complex karyotypes had poor disease prognosis.

In one embodiment, diagnosing or assessing PTCL comprises biomarker analysis. In one embodiment, a patient having a poor disease prognosis is identified by biomarker analysis wherein the presence or absence (e.g., level of) a nucleic acid or protein is detected in a biological sample from the patient (e.g., in tumor cells from a patient). A range of biomarkers are known in PTCL, including, e.g., p53, Ki-67, BCL-2, BCL-XL, CD26, EBV, MDR, CCND2, CCR4, NK-Kb, CCR3, CXCR3, PRDM1, and ALK-1.

In one embodiment, diagnosing or assessing PTCL comprises detecting chemokine receptors CXCR3 and/or CCR4 (e.g., detecting the presence or absence of CXCR3 and/or CCR4 nucleic acid or proteins, or the levels of CXCR3 and/or CCR4 nucleic acid or proteins). CXCR3 and CCR4 have been found respectively in 63% and 34% of PTCL-NOS (Percy et al., Int. Class Diseases for Oncol. (ICD-O-3), $3^{rd}$ ed., Geneva, Switzerland, World Health Organization (2000)). In one embodiment, a determination that a patient has a PTCL (e.g., PTCL cells) that is CXCR3-positive and CCR4-negative indicates that the patient has a poor disease prognosis.

Delivering anti-KIR3DL2 antibodies to a subject (either by direct administration or expression from a nucleic acid therein, such as from a pox viral gene transfer vector comprising anti-KIR3DL2 antibody-encoding nucleic acid sequence(s)) and practicing the other methods herein can be used to reduce, treat, prevent, or otherwise ameliorate any suitable aspect of cancer progression (notably PTCL progression). The methods herein can be particularly useful in the reduction and/or amelioration of tumor growth (e.g., percentage (tumor cells compared to healthy T cells), number of tumor cells in circulation) and any parameter or symptom associated therewith (e.g., biomarkers). Methods that reduce, prevent, or otherwise ameliorate such aspects of cancer progression, independently and collectively, are advantageous features.

In another aspect, a method is provided of reducing the risk of cancer progression, reducing the risk of further cancer progression in a cell population that has undergone initiation, and/or providing a therapeutic regimen for reducing cancer progression in a human patient, which comprises administering to the patient one or more first treatments (e.g., induction therapy, such as a chemotherapeutic agent or an antibody) in an amount and regimen sufficient to achieve a response (partial or complete response), and then administering an amount of an anti-KIR3DL2 antibody or related composition (or applying a combination administration method) to the patient.

In a further aspect, a method is provided of promoting remission of a PTCL in a mammalian host, such as a human patient, comprising administering a composition comprising an anti-KIR3DL2 antibody to the host, so as to promote PTCL remission in the host.

In an even further aspect, a method is provided for reducing the risk of developing a PTCL, reducing the time to onset of a cancerous condition, and/or reducing the severity of a PTCL diagnosed in the early stages, comprising administering to a host a prophylactically effective amount of an anti-KIR3DL2 antibody or related composition so as to achieve the desired physiological effect(s).

In a further aspect, a method is provided of increasing the likelihood of survival over a relevant period of a human patient diagnosed with PTCL. In another aspect, a method is provided for improving the quality of life of a PTCL patient, comprising administering to the patient a composition in an amount effective to improve the quality of life thereof. In a further aspect, methods described herein can be applied to significantly reduce the number of PTCL cells in a vertebrate host, such that, for example, the total number of PTCL cells is reduced. In a related sense, a method is provided for killing (e.g., either directly or indirectly causing the death of) PTCL cells in a vertebrate, such as a human cancer patient.

According to another embodiment, the antibody compositions may be used in combined treatments with one or more other therapeutic agents, including agents normally utilized for the particular therapeutic purpose for which the antibody is being administered, notably for the treatment of a PTCL. The additional therapeutic agent will normally be administered in amounts and treatment regimens typically used for that agent in a monotherapy for the particular disease or condition being treated.

For example, a second therapeutic agent may include one or more chemotherapeutic drugs, tumor vaccines, antibodies that bind to tumor-specific antigens on tumor cells (e.g., anti-CD30 antibodies), antibodies that induce ADCC toward tumor cells, antibodies that potentiate immune responses, etc.). Further anti-cancer agents include alkylating agents, cytotoxic antibiotics such as topoisomerase I inhibitors, topoisomerase II inhibitors, plant derivatives, RNA/DNA antimetabolites, and antimitotic agents. Examples may include cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, taxol, gemcitabine, navelbine, transplatinum, 5-fluorouracil, vincristine, vinblastine and methotrexate, or any analog or derivative variant of the foregoing.

Drugs currently used or tested for the treatment of PTCL include, inter alia, chemotherapeutic agents such as CHOP (cyclophosphamide, doxorubicin, vincristine and prednisone), anthracyclines, antifolates, conjugates such as anti-CD25 fused to *Pseudomonas* toxin, IL-2 targeting domain fused with diphtheria toxin, anti-CD30 antibody conjugated to auristatins (monomethylauristatin-E), HDAC inhibitors, lenalidomide, monoclonal antibodies such as anti-CD52, anti-VEGF (bevacizumab), anti-CD30 (adcetris), anti-CCR4, anti-CD4 (e.g., zanolimumab) and anti-CD2, nucleoside analogues such as cladribine, clofarabine, fludarabine, gemcitabine, nelarabine and pentostatin, proteosome inhibitors such as bortezomib and signaling inhibitors such as selective inhibitors of protein kinase C (e.g., enzastaurin) or syk inhibitors (e.g., R788).

In the treatment methods, the KIR3DL2-binding compound and the second therapeutic agent can be administered separately, together or sequentially, or in a cocktail. In some embodiments, the KIR3DL2-binding compound is administered prior to the administration of the second therapeutic agent. For example, the KIR3DL2-binding compound can be administered approximately 0 to 30 days prior to the administration of the second therapeutic agent. In some embodiments, a KIR3DL2-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, a KIR3DL2-binding compound is administered concurrently with the administration of the therapeutic agents. In some embodiments, a KIR3DL2-binding compound is administered after the administration of the second therapeutic agent. For example, a KIR3DL2-binding compound can be administered approximately 0 to 30 days after the administration of the second therapeutic agent. In some embodiments, a KIR3DL2-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

EXAMPLES

Example 1—Generation of KIR3DL2-Selective Antibodies

Antibodies which bind KIR3DL2 but not closely-related KIR3DL1 were generated by immunizing mice with recombinant KIR3DL2-Fc fusion protein. Supernatants (SN) of the growing hybridomas were tested by flow cytometry on Sézary Syndrome cell lines (HUT78, COU-L) and HEK-293T/KIR3DL2 Domain 0—eGFP. Potentially interesting hybridomas selected from the initial screening were cloned by limiting dilution techniques in 96-well plates. The secondary screen involved selection of hybridomas of interest by testing supernatants of the subclones by flow cytometry on HUT78, COU-L, HEK-293T/KIR3DL1 Domain 0—eGFP and HEK-293T/KIR3DL2 Domain 0—eGFP. Positive subclones were injected into mice to produce ascitis and antibodies of interest were purified before being tested in a Biacore assay using rec KIR3DL2 chips, followed by various assay formats based on binding to human KIR3DL2-expressing cells.

Sequences of the variable domains of the heavy (VH) and light (VL) chains of antibodies were amplified by PCR from the cDNA of each antibody. Sequences amplified were run on agarose gel then purified using the Qiagen Gel Extraction kit. VH and VL sequences were then subcloned into the Lonza expression vectors (Double-Gene Vectors) using the In-Fusion system (Clontech) according to the manufacturer's instructions. After sequencing, vectors containing the VH and VL sequences were prepared as maxiprep using the Promega PureYield™ Plasmid Maxiprep System. Vectors were then used for HEK-293T cell transfection using Invitrogen's Lipofectamine 2000 according to the manufacturer's instructions. Antibodies generated included, inter alia, 19H12 and 12B11.

Competition assays were conducted by flow cytometry according to the methods described. Hut-78 cells were harvested and stained in PBS 1×/BSA 0.2%/EDTA 2 mM buffer for 1H at 4° C. using 5 µg/ml of increasing concentrations of the antibodies, including 19H12, 12B11 and AZ158 (previously identified) (0.006-200 µg/ml). After two washes, staining data were acquired on a BD FACSCanto II and analyzed using FlowJo software.

Increasing concentrations of (naked) 19H12, 12B11, and AZ158 were used to shift labeled antibody bound to KIR3DL2 at the surface of HUT78 SS cell lines. Antibody AZ158 (anti-D0 domain antibody) does not compete with the KIR3DL2 antibodies 19H12 or 12B11 for binding to KIR3DL2.

Antibodies were further tested for binding to a series of KIR3DL2 mutants. Antibodies 19H12 and 12B11 did not show any loss of binding to unmutated wild-type KIR3DL2 (WTaKIR3DL2), but lost binding to mutant 11 having P179T and S181T substitutions as well as to mutant 11A1 having V178A and H180S substitutions. The principal epitope of these antibodies 19H12, 18B10 and 12B11 therefore includes residues P179, S181, V178 and/or H180. These residues at positions 179 and 181 in mutant 11 correspond to the residues present in KIR3DL1 (KIR3DL1 has T179 and T181). Residues P179 and S181 in particular are within the D1 domain of KIR3DL2 and on the opposite face of the KIR3DL2 protein of the HLA-binding regions (i.e. the HLA binding pocket). Each of antibodies 15C11, 19H12, 18B10 and 12B11 had reduced binding (full loss of binding for 15C11 and 19H12) to mutant M11A4 having substitutions E130S, H131S and R145S. These residues at positions 179 and 181 in mutant 11 correspond to the residues present in KIR3DL1 (KIR3DL1 has T179 and T181). Residues P179 and S181 in particular are within the D1 domain of KIR3DL2 and on the opposite face of the KIR3DL2 protein of the HLA-binding regions (i.e., the HLA-binding pocket). Surface-exposed residues adjacent to these mutated residues can also contribute to the epitopes of the antibodies, including for example residues N99, H100, E130, H131, F132, V178, H180, P182, Y183, and Q184 (reference to SEQ ID NO: 1) located at the surface of KIR3DL2 in the region of the P179/S181 epitope but outside of the region of the KIR3DL2 mutations which did not result in loss of binding of the antibodies (e.g., mutant 5 (residue P66) and mutant 8 (residue V127)).

Antibody 2B12 and other antibodies disclosed in the United States patent application publication 20150232556 had loss of binding to mutants having I60N and G62S substitutions and decrease in binding to mutants having P14S, S15A and H23S substitutions, but did not lose binding to any other mutants. The principal epitope of these antibodies therefore includes residues I60 and/or G62 (and the epitope optionally further includes one or more of P14, S15, and H23). Residues 60 and 62 are within the D0 domain of KIR3DL2. Residues 14, 15, 23, 60 and 61 are within the D0 domain of KIR3DL2.

Example 2—Antibodies are Able to Kill KIR3DL2 Expressing Targets Via Antibody-Dependent Cellular Cytotoxicity (ADCC)

Cell lysis through an ADCC mechanism was monitored in a radioactivity-based $^{51}$Cr release experiment (the level of radioactivity released from the preloaded target cells being proportional to their death). One million target cells were loaded with $^{51}$Cr for 1 hour at 37° C. and washed 3 times. 3,000 cells were seeded per well (U-shaped bottom 96-well plates) and test mAbs were added at 10 or 20 µg/ml final concentration (or increasing concentrations if dose-response relationship is studied). Effector cells were added at a defined effector:target ratio (in general 10:1) and the mixture was incubated at 37° C. for 4 h. Supernatant is analyzed on a Lumaplate apparatus.

Anti-KIR3DL2 mAbs was tested at the same final concentration (10 µg/ml) to kill KIR3DL2-transfected B221 target cells. The mAbs, including 19H12, were effective in mediating ADCC against KIR3DL2-expressing B221 targets.

Example 3—Activity in Mouse Xenograft Models of KIR3DL2-Expressing Human Tumors Tumor cell lines B221 and RAJI were made to express human KIR3DL2. Immune compromised mice used for B221-KIR3DL2 and RAJI-KIR3DL2 models were NOD-SCID purchased from Charles River Laboratories. In the following models, 5 million human B221-KIR3DL2 or RAJI-KIR3DL2 tumor cells (in 100 µl PBS as vehicle) were engrafted IV on Day 0 (D0), i.e., 1 day before treatment initiation (D1). From D1, mice were treated IV with different doses of anti-KIR3DL2 mAbs (doses were adapted to mouse body weight) diluted in PBS, 2 injections per week for the duration of the whole experiment.

Control groups included, depending on the experiment:
PBS/placebo-treated mice as a control of normal/unaffected tumor growth; and
mice injected with the same dose of isotype control-matched mAbs directed against an irrelevant antigen.

Mice were weighed and observed for clinical signs every 2 to 5 days depending on the model. Percent of body weight changes were calculated as compared to body weight at D0 before tumor engraftment or to the highest body weight reached during the experiment. Mouse deaths or important weight losses were recorded and used to draw survival Kaplan-Meier curves and calculate improvement in survival as compared to control groups of mice.

The efficacy of IgG2b isotype murine anti-KIR3DL2 19H12 antibodies (given at 300 µg/mouse, twice a week) was separately tested against SC B221-KIR3DL2 xenografts or RAJI-KIR3DL2 xenografts (n=6 NOD-SCID mice per group). Animals treated with anti-KIR3DL2 antibodies showed an increase in survival in comparison to mice treated with isotype control-matched mAbs.

Example 4—Improved Detection Methods Reveal KIR3DL2-Positive Tumors

Tumor biopsies from RAJI-KIR3DL2 models and RAJI-KIR3DL2 cell lines were obtained and staining was performed on frozen samples using AZ158 antibody (see WO2010/081890) or antibodies 12B11 (see Example 1). KIR3DL2 was stained with anti-KIR3DL2 antibody by DAB chromogenic detection according to standard protocols, adapted for immunostaining with BenchMark XT (Ventana, Roche). For all staining control isotype (mIgG1) and control DAB were performed. Surprisingly, while AZ158 was negative, tumors were positive when using 12B11 antibody at the same concentration (5 µg/ml) of antibody (see FIG. 1). Raising concentrations of antibody AZ158 (to 50 µg/ml) generated extensive background staining that did not allow tumor samples to be differentiated from healthy tissue.

Figure 2:
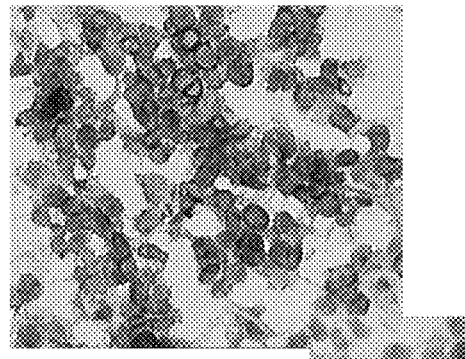
FIG. 2 shows staining of frozen tissue sections from cancer patients previously stained with AZ158, re-examined using antibody 12B11. Biopsies that had been KIR3DL2-negative with AZ158 were stained with 12B11 (i.e., becoming KIR3DL2-positive).
Figure 2:
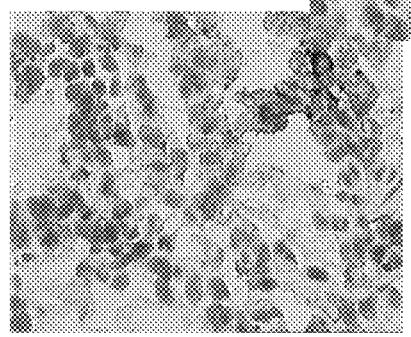

Next, tumor biopsies from cancer patients previously stained with AZ158 were re-examined using antibody 12B11. Biopsies that had been KIR3DL2-negative with AZ158 were stained with 12B11 (i.e., becoming KIR3DL2-positive). Results are shown in FIG. 2.

Example 5—KIR3DL2 is Expressed in PTCL

Tumor biopsies from PTCL patients were obtained and staining was performed on frozen samples. KIR3DL2 was stained with anti-KIR3DL2 antibody 12B11 (mIgG1) by DAB chromogenic detection according to standard protocols, adapted for immunostaining with BenchMark XT (Ventana, Roche). For all staining control isotype (mIgG1) and control DAB were performed. CD30 was additionally stained. Tumors 3, 4 and 5 were from the same patient. Tumors 1-5 are from patients having PTCL not otherwise specified. Tumors 6-8 are samples of mycosis fungoides, a cutaneous T cell lymphoma (CTCL).

Results are shown in Table A below (LN=lymph node). Tumor sample characteristics are shown in Table B. PTCL from each of the samples from the patient from which tumor samples 3, 4 and 5 were obtained had strong membranar staining, with a high percentage of cells being KIR3DL2-positive. We also note that the patient from which samples 3-5 were obtained had advanced (stage IV) disease while samples 1, 2, 6, 7 and 8 represented less advanced disease (stage I or II); all had either no staining or low percentages of KIR3DL2+ tumor cells. It is possible that while some tumors are capable of expressing KIR3DL2 at high levels and are thus suitable for targeting with a KIR3DL2 binding agent, tumor cells may acquire the NK marker KIR3DL2 at more advanced stages of disease, or more aggressive disease. KIR3DL2 may therefore be a particularly suitable target for treatment of aggressive PTCLs and/or advanced disease. Additionally, patients with earlier stages of disease may benefit from treatment or diagnostic assays using KIR3DL2 binding agents to identify patients having prominent expression of KIR3DL2 on the surface of tumor cells. Additionally, KIR3DL2-positive PTCL-NOS tumors were found to include CD30 negative cases; KIR3DL2 may therefore furthermore represent a therapeutic target when anti-CD30 antibodies cannot be used (or when tumors are resistant to anti-CD30 antibodies).

Example 6—KIR3DL2 is Expressed in Samples from ALCL and Ortho-Visceral Extranodal Disease (NK/T Lymphoma and EATL)

MEC04 and SNK6 NK/T lymphoma cells were stained for KIR3DL2 expression using flow cytometry (FACS), together with characterization of various cell surface markers. KIR3DL2 was stained with anti-KIR3DL2 antibody linked to phycoerythrin (PE). Additional markers evaluated were hCD56 PE, hCD183/CXCR3 PE, hCD3 PE, hCD4 PE, hCD8 PE and CD54/ICAM PE. Cells were harvested and stained using PE-labeled antibodies. After two washes, stainings were acquired on a BD FACS Canto II and analyzed using the FlowJo software.

Figure 3:
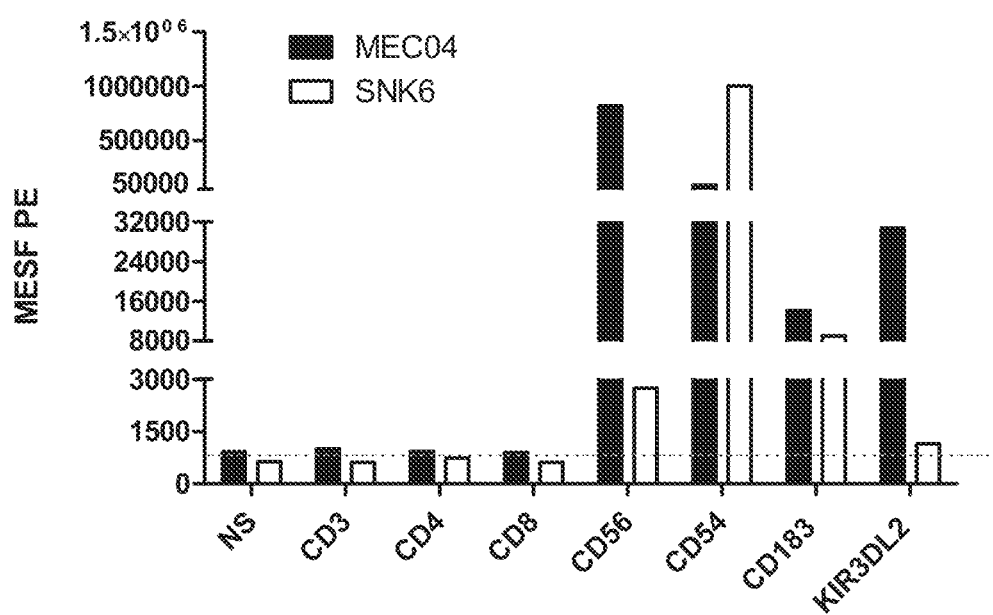
FIG. 3 shows staining by anti-KIR3DL2 antibody on NK/T lymphoma cells, nasal type. The figure additionally shows that the KIR3DL2-positive cells express CD183 (CXCR3), CD56 and CD54 (ICAM).

Results are shown in FIG. 3. Anti-KIR3DL2 antibody showed strong staining on the MEC04 cells. MEC04 cells were additionally positive for staining with CD183 (CXCR3), CD56 and CD54 (ICAM), but not CD3, CD4 or CD8 (the most common phenotype of extranodal NK/T lymphomas are surface CD3− and CD56+).

NK/T lymphoma cells, and in particular extranodal NK/T cell lymphoma, nasal type, can therefore express KIR3DL2 at significant levels, thereby providing the possibility to treat such disease with anti-KIR3DL2 antibodies. Additionally, KIR3DL2-positive NK/T lymphoma tumors were found to express CD183 (CXCR3), CD56 and CD54 (ICAM), which may permit administration of anti-KIR3DL2 in poor-prognosis patients, for example those having CXCR3 expression typically associated with poor disease prognosis.

Studies were carried out by immunohistochemistry (IHC) to provide confirmation on patient samples and for different indications, by staining primary tumor cells from human patients in frozen tissue sections with labeled anti-KIR3DL2 antibody. Briefly, cell lines known to be positive and negative for KIR3DL2 expression were used as positive and negative controls, respectively. In NK/T lymphomas, nasal type, 6 patient samples were tested, of which 5 samples were interpretable. 2 interpretable samples were positively stained and 3 were not, confirming that NK/T lymphomas express KIR3DL2. In samples from patients diagnosed with enteropathy-associated T cell lymphoma (EATL), of 5 interpretable samples, 2 were positively stained and 3 were negative for staining, confirming that EATL cells can express KIR3DL2. In samples from patients diagnosed with anaplastic large cell lymphoma (ALCL), of 4 interpretable patient samples, 2 were positively stained and 2 were negative for staining, confirming that ALCL cells can express KIR3DL2. Of the ALCL that stained positive for KIR3DL2, samples included both ALK+ and ALK−.

TABLE A

| Tumor sample | KIR3DL2 Staining | CD30 staining |
|---|---|---|
| Tumor 1: LN/Lymphoma peripheral T cells | Positive | Negative |
| Tumor 2: Testis/Lymphoma peripheral T cells | Negative | Negative |
| Tumor 3: Spleen/Lymphoma peripheral T cells | Negative | Positive |
| Tumor 4: Spleen/Lymphoma peripheral T cells | Negative | Positive |
| Tumor 5: Spleen/Lymphoma peripheral T cells | Negative | Positive |
| Tumor 6: LN/Mycosis fungoides | Positive | Positive |
| Tumor 7: LN/Mycosis fungoides | Positive | Positive |
| Tumor 8: LN/Mycosis fungoides | Positive | Positive |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a", "an", "the" and similar referents in the context of describing the invention is to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

The description herein of any aspect or embodiment of the invention using terms such as "comprising", "having", "including", or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples or exemplary language (e.g., "such as") provided herein is intended merely to better illuminate the invention and does not pose a limitation on the scope of the invention unless otherwise claimed. No language in the specification should be construed as indicating any non-claimed element as essential to the practice of the invention.

TABLE B

| Sample | Tissue type | Appearance | Pathology diagnosed | Tumor stage (minimum) | % normal | % lesion | % tumor | % nercosis |
|---|---|---|---|---|---|---|---|---|
| 1 | Lymphoid tissue/ lymphatic ganglion | Tumoral | PTCL (unspecified) | I | 5 | 0 | 90 | 0 |
| 2 | Lymphoid tissue/ testicle | Tumoral | PTCL-NOS (unspecified) | IE | 10 | 0 | 60 | 0 |
| 3 | Lymphoid tissue/ spleen | Tumoral | PTCL-NOS (unspecified) | IV | 10 | 0 | 40 | 0 |
| 4 | Lymphoid tissue/ spleen | Tumoral | PTCL-NOS (unspecified) | IV | 5 | 0 | 90 | 0 |
| 5 | Lymphoid tissue/ spleen | Tumoral | PTCL-NOS (unspecified) | IV | 50 | 0 | 50 | 0 |
| 6 | Lymphoid tissue/ lymphatic ganglion | Tumoral | Mycosis fungoides | II | 0 | 0 | 70 | 20 |
| 7 | Lymphoid tissue/ lymphatic ganglion | Tumoral | Mycosis fungoides | II | 0 | 0 | 80 | 10 |
| 8 | Lymphoid tissue/ lymphatic ganglion | Tumoral | Mycosis fungoides | II | 0 | 0 | 80 | 10 |

We claim:

1. A method of treating an peripheral T-cell lymphoma not otherwise specified (PTCL-NOS), comprising administering to an individual suffering from said PTCL-NOS a therapeutically active amount of an antibody that binds a KIR3DL2 polypeptide comprising the amino acid sequence of SEQ ID NO: 1 and that further: i) directs ADCC toward a KIR3DL2-expressing cell, or ii) delivers a cytotoxic agent to a KIR3DL2-expressing cell.

2. The method of claim 1, wherein the treatment comprises:
   a) determining the KIR3DL2 polypeptide status of malignant cells within the individual having an PTCL-NOS, and
   b) upon a determination that the individual has a KIR3DL2 polypeptide comprising the amino acid sequence of SEQ ID NO: 1 expressed on the surface of malignant cells, administering to the individual said antibody that binds a KIR3DL2 polypeptide and that further: i) directs ADCC toward the KIR3DL2-expressing malignant cells and/or ii) delivers a cytotoxic agent to the KIR3DL2-expressing malignant cells.

3. The method of claim 1, wherein the anti-KIR3DL2 antibody directs ADCC toward a KIR3DL2-expressing cell.

4. The method of claim 3, wherein the antibody comprises an amino acid modification that enhances binding to a human Fcγ receptor.

5. The method of claim 3, wherein the anti-KIR3DL2 antibody binds human KIR3DL2 but does not bind to human KIR3DL1.

6. The method of claim 1, wherein the antibody is linked to a cytotoxic agent.

7. The method of claim 1, wherein the anti-KIR3DL2 antibody binds human KIR3DL2 but does not bind to human KIR3DL1.

8. The method of claim 1, wherein the KIR3DL2 antibody comprises an antibody variable region comprising:
   a) a heavy chain variable region comprising a heavy chain CDR1 (hCDR1) comprising SEQ ID NOs: 7, 8 or 9, a heavy chain CDR2 (hCDR2) comprising SEQ ID NO: 10 or 11, a heavy chain CDR3 (hCDR3) comprising SEQ ID NO: 12 and a light chain variable region comprising a light chain CDR1 (LCDR1) comprising SEQ ID NO: 13, a light chain CDR2 (LCDR2) comprising SEQ ID NO: 14, and a light chain CDR3 (LCDR3) comprising SEQ ID NO: 15;
   b) a heavy chain variable region comprising a heavy chain CDR1 (hCDR1) comprising SEQ ID NO: 18, 19 or 20, a heavy chain CDR2 (hCDR2) comprising SEQ ID NO: 21 or 22, a heavy chain CDR3 (hCDR3) comprising SEQ ID NO: 23 and a light chain variable region comprising a light chain CDR1 (LCDR1) comprising SEQ ID NO: 24, a light chain CDR2 (LCDR2) comprising SEQ ID NO: 25, and a light chain CDR3 (LCDR3) comprising SEQ ID NO: 26;
   c) a heavy chain variable region comprising a heavy chain CDR1 (hCDR1) comprising SEQ ID NO: 34, a heavy chain CDR2 (hCDR2) comprising SEQ ID NO: 38, a heavy chain CDR3 (hCDR3) comprising SEQ ID NO: 39 and a light chain variable region chain comprising a light chain CDR1 (LCDR1) comprising SEQ ID NO: 40, a light chain CDR2 (LCDR2) comprising SEQ ID NO: 41, and a light chain CDR3 (LCDR3) comprising SEQ ID NO: 42; or
   d) a heavy chain variable region comprising a heavy chain CDR1 (hCDR1) comprising SEQ ID NO: 35, a heavy chain CDR2 (hCDR2) comprising SEQ ID NO: 37, a heavy chain CDR3 (hCDR3) comprising SEQ ID NO: 39 and a light chain variable region comprising a light chain CDR1 (LCDR1) comprising SEQ ID NO: 40, a light chain CDR2 (LCDR2) comprising SEQ ID NO: 41, and a light chain CDR3 (LCDR3) comprising SEQ ID NO: 42.

9. The method of claim 8, wherein the KIR3DL2 antibody comprises a heavy chain variable region comprising a heavy chain CDR1 (hCDR1) comprising SEQ ID NOs: 7, 8 or 9, a heavy chain CDR2 (hCDR2) comprising SEQ ID NO: 10 or 11, a heavy chain CDR3 (hCDR3) comprising SEQ ID NO: 12 and a light chain variable region comprising a light chain CDR1 (LCDR1) comprising SEQ ID NO: 13, a light chain CDR2 (LCDR2) comprising SEQ ID NO: 14, and a light chain CDR3 (LCDR3) comprising SEQ ID NO: 15.

10. The method of claim 8, wherein the KIR3DL2 antibody comprises a heavy chain variable region comprising a heavy chain CDR1 (hCDR1) comprising SEQ ID NO: 18, 19 or 20, a heavy chain CDR2 (hCDR2) comprising SEQ ID NO: 21 or 22, a heavy chain CDR3 (hCDR3) comprising SEQ ID NO: 23 and a light chain variable region comprising a light chain CDR1 (LCDR1) comprising SEQ ID NO: 24, a light chain CDR2 (LCDR2) comprising SEQ ID NO: 25, and a light chain CDR3 (LCDR3) comprising SEQ ID NO: 26.

11. The method of claim 8, wherein the KIR3DL2 antibody comprises an antibody variable region comprising a heavy chain variable region comprising a heavy chain CDR1 (hCDR1) comprising SEQ ID NO: 34, a heavy chain CDR2 (hCDR2) comprising SEQ ID NO: 38, a heavy chain CDR3 (hCDR3) comprising SEQ ID NO: 39 and a light chain variable region comprising a light chain CDR1 (LCDR1) comprising SEQ ID NO: 40, a light chain CDR2 (LCDR2) comprising SEQ ID NO: 41, and a light chain CDR3 (LCDR3) comprising SEQ ID NO: 42.

12. The method of claim 8, wherein the KIR3DL2 antibody comprises a heavy chain variable region comprising a heavy chain CDR1 (hCDR1) comprising SEQ ID NO: 35, a heavy chain CDR2 (hCDR2) comprising SEQ ID NO: 37, a heavy chain CDR3 (hCDR3) comprising SEQ ID NO: 39 and a light chain variable region comprising a light chain CDR1 (LCDR1) comprising SEQ ID NO: 40, a light chain CDR2 (LCDR2) comprising SEQ ID NO: 41, and a light chain CDR3 (LCDR3) comprising SEQ ID NO: 42.

13. A method of treating an peripheral T-cell lymphoma not otherwise specified (PTCL-NOS), comprising administering to an individual suffering from said PTCL-NOS a therapeutically active amount of an antibody that binds a KIR3DL2 polypeptide comprising the amino acid sequence of SEQ ID NO: 1 and that further directs ADCC toward a KIR3DL2-expressing cell, wherein the KIR3DL2 antibody comprises an antibody variable region comprising a heavy chain CDR1 (hCDR1) comprising SEQ ID NO: 35, a heavy chain CDR2 (hCDR2) comprising SEQ ID NO: 37, a heavy chain CDR3 (hCDR3) comprising SEQ ID NO: 39 and a light chain variable region comprising a light chain CDR1 (LCDR1) comprising SEQ ID NO: 40, a light chain CDR2 (LCDR2) comprising SEQ ID NO: 41, and a light chain CDR3 (LCDR3) comprising SEQ ID NO: 42.

* * * * *

UNITED STATES PATENT AND TRADEMARK OFFICE
CERTIFICATE OF CORRECTION

PATENT NO. : 12,084,498 B2
APPLICATION NO. : 17/388052
DATED : September 10, 2024
INVENTOR(S) : Cécile Bonnafous, Hélène Sicard and Renaud Buffet Page 1 of 1

It is certified that error appears in the above-identified patent and that said Letters Patent is hereby corrected as shown below:

In the Specification

Column 13,
Line 63, "(e.g., a, 6, c and p" should read --(e.g., α, δ, ε and μ--.

Column 42,
Line 24, "CD30+" should read --$CD30^+$--.

Signed and Sealed this
Twenty-first Day of October, 2025

John A. Squires
*Director of the United States Patent and Trademark Office*